United States Patent [19]

Sone et al.

[11] Patent Number: 5,429,766
[45] Date of Patent: * Jul. 4, 1995

[54] DETERGENT COMPOSITION CONTAINING ALKALINE PULLYLANASE ENZYME

[75] Inventors: Taeko Sone; Masaki Tosaka, both of Utsunomiya; Katsuhisa Saeki, Kawachi; Katsutoshi Ara; Katsuhiko Deguchi, both of Utsunomiya; Kazuaki Igarashi, Ichikaimachi, all of Japan

[73] Assignee: Kao Corporation, Tokyo, Japan

[*] Notice: The portion of the term of this patent subsequent to Sep. 15, 2009 has been disclaimed.

[21] Appl. No.: 139,148

[22] Filed: Oct. 21, 1993

Related U.S. Application Data

[60] Division of Ser. No. 960,262, Oct. 13, 1992, which is a continuation of Ser. No. 681,007, Apr. 5, 1991, abandoned.

[30] Foreign Application Priority Data

Apr. 5, 1990 [JP] Japan .................. 2-91179
Apr. 6, 1990 [JP] Japan .................. 2-91563

[51] Int. Cl.⁶ .................. C11D 3/386; C11D 1/00; C12N 9/44
[52] U.S. Cl. .................. 252/174.12; 252/DIG. 12; 435/210; 435/832
[58] Field of Search .................. 252/174.12, DIG. 12; 435/210, 832

[56] References Cited

U.S. PATENT DOCUMENTS

| | | | |
|---|---|---|---|
| 5,030,377 | 9/1991 | Sone et al. | 252/174.12 |
| 5,147,795 | 9/1992 | Ara et al. | 435/210 |
| 5,147,796 | 9/1992 | Ara et al. | 435/210 |
| 5,316,691 | 5/1994 | Sone et al. | 252/174.12 |

FOREIGN PATENT DOCUMENTS

| | | |
|---|---|---|
| 0418835 | 3/1991 | European Pat. Off. |
| 60-186282 | 9/1985 | Japan |
| 0368341 | 5/1990 | Japan |
| 0450627 | 10/1991 | Japan |
| 2228945 | 9/1990 | United Kingdom |

*Primary Examiner*—John S. Maple
*Assistant Examiner*—Kery Fries
*Attorney, Agent, or Firm*—Oblon, Spivak, McClelland, Maier & Neustadt

[57] ABSTRACT

A novel detergent composition containing an alkaline pullulanase is disclosed. The alkaline pullulanase has its optimum pH in an alkaline range and not deactivated by surfactants. Further it has strong resistance to almost all detergent components such as chelating agents, protease, etc. The the detergent composition of this invention has excellent detergency especially against starch soils.

4 Claims, 9 Drawing Sheets

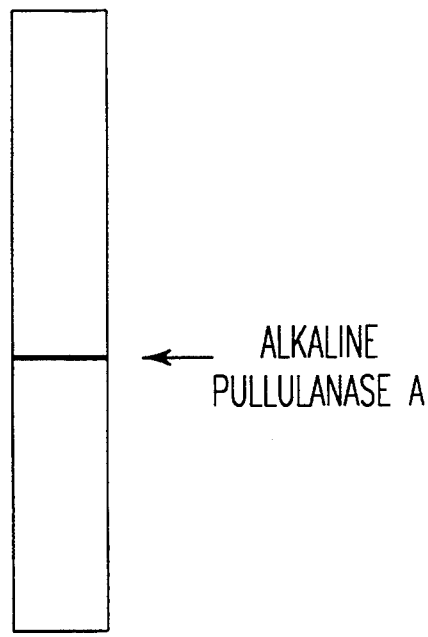
FIG. 5 ALKALINE PULLULANASE A
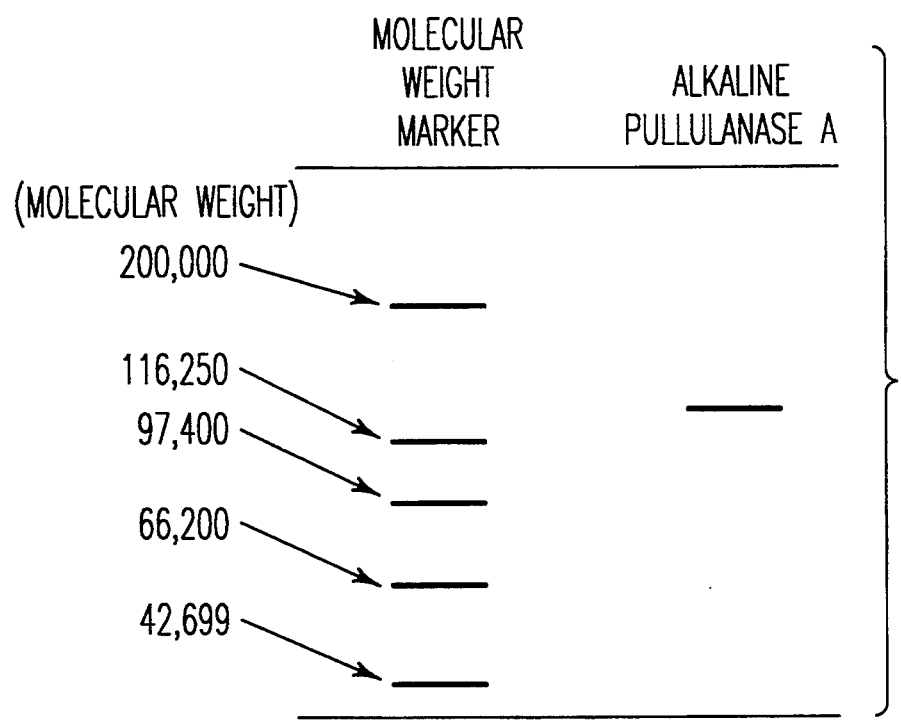
FIG. 6

DETERGENT COMPOSITION CONTAINING ALKALINE PULLYLANASE ENZYME

This is a division, of application Ser. No. 07/960,262, filed on Oct. 13, 1992, which is a continuation of application Ser. No. 07/681,007, filed on Apr. 5, 1991, abandoned.

BACKGROUND OF THE INVENTION

1. Field of the Invention

This invention relates to a detergent composition containing alkaline pullulanase which has excellent detergency especially against starch soil.

2. Description of the Background Art

It is a known art that enzymes are compounded into a detergent composition The enzymes in the detergent composition act as a wash-aiding agent. They decompose or denature various kinds of soil and stain adhered to clothes, fats and oils, proteins, starch and the like remained on the dish surface to facilitate removal of the stains.

Heretofore, α-amylase has been used in order to remove starch soils. Detergency against starch soils is improved by soaking the washes in a washing solution containing α-amylase for a reasonably long time.

The inventors of the present invention found that a certain type of pullulanase effectively acted on starch soils adhered firmly to dishes and fibers, and enabled to improve the detergency remarkably (Japanese Patent Application Laid-Open (Kokai) No. 132192/1990).

However, almost all naturally occurring pullulanases are classified into neutral or acidic pullulanases which exhibit the maximal and stable enzymatic activity under the neutral or acidic pH conditions. Very few pullulanases exhibit the maximal activity or alkali-resistance in the alkaline pH range, which are suitable for a detergent composition for dishes or clothes.

An alkaline pullulanase in this invention means a pullulanase having an optimum pH in the alkaline range. An alkali-resistant pullulanase in this invention means a pullulanase having an optimum pH in the neutral to acidic range, and exhibiting still sufficient degree of activities even in the alkaline range when compared to the activity at its optimum pH while retaining a good stability. The terms 'neutral' and 'alkaline' are defined as the pH ranges of 6–8 and not less than 8, respectively.

Only alkaline pullulanase known heretofore is that disclosed in Japanese Patent Publication (Kokoku) No. 27786/1978. The above alkaline pullulanase is an enzyme having its optimum pH in the alkaline range and also having a wider substrate specificity than conventionally known pullulanases. However, since its optimum pH is in the weak alkaline range of 8–9, it is not applicable to a detergent component. In addition, the above pullulanase has disadvantages that the enzyme is unstable and has low productivity. Therefore, the above pullulanase is not suitable for the industrial fermentative production.

In view of this situation, the present inventors have carried out extensive studies in order to obtain pullulanases suitable as a detergent component, and, as a result, found that a detergent composition having detergency against starch soil was obtained by compounding an alkaline pullulanase which has its optimum pH in a high pH range and is not deactivated by surfactants. This finding has led to the completion of the present invention.

SUMMARY OF THE INVENTION

Accordingly, an object of the present invention is to provide a novel detergent composition comprising an alkaline pullulanase having its optimum pH in the alkaline range and being stable against surfactants.

Other objects, features, and advantages of the invention will hereinafter become more apparent from the following description.

BRIEF DESCRIPTION OF THE DRAWINGS

FIG. 5 shows the results of electrophoresis of the alkaline pullulanase A used in the present invention.

FIG. 6 shows a SDS electrophoresis profile of the alkaline pullulanase A used in the present invention.

FIG. 18 is a SDS electrophoresis profile of the alkaline pullulanase B having α-amylase activity used in the present invention.

DETAILED DESCRIPTION OF THE INVENTION AND PREFERRED EMBODIMENTS

Figure 1:
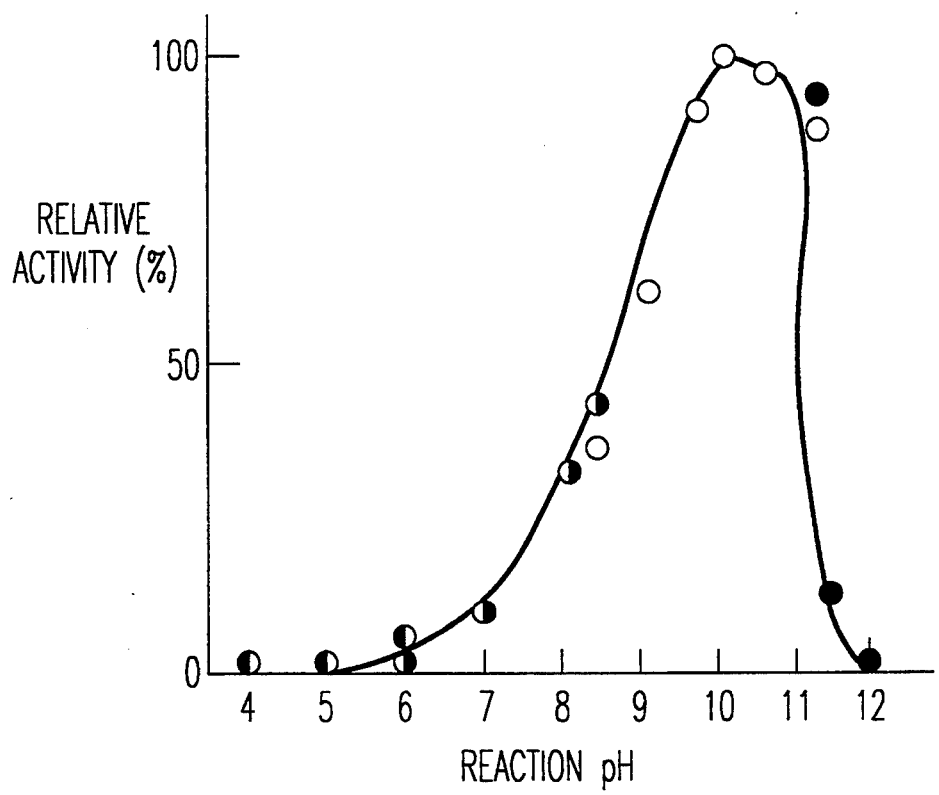
FIG. 1 shows the relation of reaction pH vs. relative activity of the alkaline pullulanase A used in the present invention.

Alkaline pullulanases used in the present invention are not specifically limited so far as they have their optimum pH in a high alkaline range and are not deactivated by surfactants.

Such alkaline pullulanases include an alkaline pullulanase A and an alkaline pullulanase B having the following characteristics:

Alkaline Pullulanase A

1) Action

Decomposes α-1,6 glucoside linkage of pullulan to produce maltotriose. Hydrolyzes α-1,6 glucoside linkage of starch, amylopectin, glycogen, or their partial decomposition products.

2) Substrate specificity

Hydrolyzes a branch structure having a degree of polymerization which is not less than the degree of polymerization of maltose among sugars having a branch of $\alpha$-1,6 glucoside linkage.

3) Working pH and optimum pH range

The working pH is in the range of 5-11 with the optimum pH range of 9.5-11.

4) pH stability

Quite stable in the pH range of 8-10, and has relative activity not less than 50% even in the pH range of 7-10.5 (treatment: 45° C., 10 minutes).

5) Working temperature and optimum temperature

Acts at a wide temperature range of 10°-60° C. with an optimum temperature being about 50° C.

6) Thermal stability

Quite stable up to 40° C. when treated in 10 mM glycine-NaCl-NaOH buffer solution (pH 9.5) for 30 minutes.

7) Effects of surfactants

Surfactants such as linear alkylbenzene sulfonate, sodium alkyl sulfate, sodium polyoxyethylene alkylsulfate, sodium $\alpha$-olefin sulfonate, sodium $\alpha$-sulfonated fatty acid ester, sodium alkyl sulfonate, sodium dodecyl sulfate, soaps, and Softanol (trade-mark) give almost no adverse effect on activity.

Alkaline Pullulanase B

Has $\alpha$-amylase activity. In more detail, has the following characteristics:

1) Action

Acts on pullulan and soluble starch to produce mainly maltotriose from pullulan and mainly maltotetraose and maltopentaose from soluble starch. Acts also on glycogen to produce maltotetraose and maltopentaose.

2) Substrate specificity

Acts on pullulan, soluble starch, and glycogen.

3) Working pH and optimum pH

The working pH on pullulan is in the range of 5-12 with the optimum pH in the range of 8.5-10.

The working pH on soluble starch in the range of 4-12 with the optimum pH in the range of 7-9.5.

4) pH stability

Stable in the pH range of 6-10.5 against pullulan, and in the pH range of 4-12 against soluble starch (treatment: 45° C., 10 minutes).

5) Working temperature and optimum temperature

Acts on pullulan and soluble starch at wide temperature range of 10°-65° C. with an optimum temperature being about 50° C.

6) Thermal stability

Quite stable up to 45° C. when treated in 10 mM glycine-NaCl-NaOH buffer solution (pH 9.5) for 30 minutes.

7) Effects of surfactants

Surfactants such as linear alkylbenzene sulfonate, sodium polyoxyethylene alkyl sulfate, sodium $\alpha$-olefin sulfonate, sodium $\alpha$-sulfonated fatty acid ester, sodium alkyl sulfonate, sodium dodecyl sulfate, soaps, and Softanol (trade-mark) give almost no adverse effect on activity.

The alkaline pullulanase A used in the present invention is produced, for example, by Bacillus sp. KSM-AP 876 (FERM BP-3049) which is a kind of alkalophilic microorganism.

This microorganism has the mycological characteristics which will be described below.

The following 21 culture media (Media 1 to 21) were used for the classification of strains. They all contain 0.5% by weight of sterilized sodium carbonate ($Na_2CO_3$).

Compositions of the Culture Media Used (% by Weight)

Medium 1: nutrient broth, 0.8 ; agar powder (manufactured by Wako Pure Chemical Co.), 1.5

Medium 2: nutrient broth, 0.8

Medium 3: nutrient broth, 0.8; gelatin 20.0; agar powder (manufactured by Wako Pure Chemical Co.), 1.5

Medium 4: Bacto litmus milk, 10.5

Medium 5: nutrient broth, 0.8; $KNO_3$, 0.1

Medium 6: Bacto peptone, 0.7; NaCl, 0.5; glucose, 0.5

Medium 7: SIM agar medium (manufactured by Eiken Kagaku Co.), an amount indicated.

Medium 8: TSI agar medium (manufactured by Eiken Kagaku Co.), an amount indicated.

Medium 9: yeast extract, 0.5; bacto peptone, 1.5; $K_2HPO_4$, 0.1; $MgSO_4.7H_2O$, 0.02; soluble starch, 2.0; agar powder (manufactured by Wako Pure Chemical Co.), 1.5

Medium 10: Koser's medium (manufactured by Eiken Kagaku Co.), an amount indicated.

Medium 11: Christensen's medium (manufactured by Eiken Kagaku Co.), an amount indicated.

Medium 12: contains compositions (1) and (2) indicated below to which are added nitrogen sources consisting of sodium nitrate, sodium nitrite, ammonium chloride, and ammonium phosphate at an amount of 0.25%, 0.2025%, 0.158%, and 0.195% by weight respectively in the medium.

(1) yeast extract, 0.05; $Na_2SO_4$, 0.1; $KH_2PO_4$, 0.1; glucose, 1.0

(2) yeast extract, 0.05; $Na_2SO_4$, 0.1; $KH_2PO_4$, 0.1; glucose, 1.0; $CaCl_2.2H_2O$, 0.05; $MnSO_4.4-6H_2O$, 0.01; $FeSO_4.7H_2O$, 0.001; $MgSO_4.7H_2O$, 0.02

Medium 13: King A medium 'Eiken' (manufactured by Eiken Kagaku Co.), an amount indicated.

Medium 14: King B medium 'Eiken' (manufactured by Eiken Kagaku Co.), an amount indicated.

Medium 15: urea medium 'Eiken' (manufactured by Eiken Kagaku Co.), an amount indicated.

Medium 16: cytochrome-oxidase test filter paper (manufactured by Nippon Pharmaceutical Co.)

Medium 17: 3% aqueous hydrogen peroxide

Medium 18: Bacto peptone, 0.5; yeast extract, 0.5; $K_2HPO_4$, 0.1; glucose, 1.0; $MgSO_4.7H_2O$, 0.02

Medium 19: Bacto peptone, 2.7; NaCl, 5.5; $K_2HPO_4$, 0.3; glucose, 0.5; bromothymol blue, 0.06; agar powder (manufactured by Wako Pure Chemical Co.), 1.5

Medium 20: $(NH_4)_2HPO_4$, 0.1; KCl, 0.02 ; $MgSO_4.7H_2O$, 0.02; yeast extract, 0.05; sugar, 1.0

Medium 21: casein, 0.5; yeast extract, 0.5; glucose, 1.0; $K_2HPO_4$, 0.1; $MgSO_4.7H_2O$, 0.02; agar powder (manufactured by Wako Pure Chemical Co.), 1.5

Mycological Characteristics a) Observation Under Microscope

Cells are rods of a size of 1.0-2.2 $\mu m \times 2.2$-4.4 $\mu m$, with an elliptical endospore (0.8-1.0 $\mu m \times 1.0$-1.8 $\mu m$) forming at their subterminals. They have flagella and are motile. Gram's staining indefinite. Acid fastness is negative.

b) Growth in Various Culture Media
1) Broth agar plate culture (Medium 1) Growth of cells is good. Colony has a circular shape, with its surface being smooth and its peripheral end being smooth or wavy. The color of the colony is milky semitransparent, and glossy.
2) Broth agar slant culture (Medium 1) Cells can grow. Colony has a cloth-spreading shape, with a color of the colony being milky, semitransparent, and glossy.
3) Broth liquid culture (Medium 2) Cells can grow.
4) Stab culture in broth-gelatin (Medium 3) growth of cells is good. Liquefaction of gelatin is observed.
5) Litmuth milk medium (Medium 4) Milk coagulation and peptonization are not observed. Litmuth discoloration is indeterminable because the medium is an alkaline medium.

c) Physiological Characteristics
1) Nitrate reduction and denitrification (Medium 5) Nitrate reduction is positive. Denitrification is negative.
2) MR test (Medium 6) Indeterminable because the medium is an alkaline medium.
3) VP test (Medium 6) Negative.
4) Production of indole (Medium 7) Negative.
5) Production of hydrogen sulfide (Medium 8) Negative
6) Hydrolysis of starch (Medium Positive
7) Utilization of citric acid Negative in Koser's medium (Medium 10), and indeterminable in Christensen's medium (Medium 11).
8) Utilization of inorganic nitrogen sources (Medium 12) Nitrate, ammonium salts, and nitrite are all utilized.
9) Discoloration (Medium 13, Medium 14) Negative.
10) Urease (Medium 15) Negative.
11) Oxidase (Medium 16) Indeterminable between positive and negative.
Catalase (Medium 17) Positive.
13) Growth range (Medium 18) Growth temperature: 20°–40° C. Optimum growth temperature: 30°–35° C. Growth pH range: 7–10.5 Optimum growth pH: 10
14) Behavior toward oxygen Aerobic.
15) O-F test (Medium 19) Discoloration is indeterminable because the medium is an alkaline medium. Cells can grow only under aerobic conditions.
16) Sugar utilization (Medium 20) L-Arabinose, D-Xylose, D-glucose, D-mannose, D-fractose, D-galactose, maltose, sucrose, lactose, trehalose, D-sorbitol, D-mannitol, glycerol, starch, salicin, D-ribose and dextrin are utilized.
17) Growth in a medium containing sodium salt (modification of Medium 1) Cells can grow in the presence of 5% of NaCl, but cannot grow in the presence of 7% sodium chloride.
18) Hydrolysis of casein (Medium 21) Positive.

Based on the above mycological characteristics, the strain of the present invention was examined referring to Bergey's Mannual of Determinative Bacteriology, 8th ed., and 'The Genus Bacillus' Ruth, E. Gordon, Agriculture Handbook No. 427, Agricultural Research Service, U.S. Department of Agriculture Washington D.C., (1973), and determined as an asporogenas rod-shaped microorganism belonging to the genus Bacillus The strain did not grow in the neutral pH range, but drew mostly in the highly alkaline range. From this fact, the strain of the present invention was classified as an alkalopholic microorganism which was demonstrated by Horikoshi and Akiba [Alkalophilic Microorganism, Japan Scientific Society Press (Tokyo), 1982]. The strain of the present invention is thus distinguished from a group of microorganisms belonging to the denus Bacillus which grows in a neutral pH range.

The strain of the present invention has mycologically different characteristics from those of any conventionally known 'alkalophilic Baccillus'. Accordingly, the strain of the present invention was determined as a novel strain and named Baccillus sp. KSM-AP 1876, which was deposited with Fermentation Research Institute, Agency of Industrial Science and Technology as FERM BP-3049.

The production of an alkaline pullulanase A used in the present invention can be processed by inoculating the above microoganisms according to the conventional cultivating methods. It is desirable to add a suitable amount of carbon and nitrogen sources which the microorganism can utilize in the medium. There are no specific limitations as to carbon and nitrogen sources. Exemplary organic nitrogen sources. include corn gluten meal, soybean flour, corn steep liquor, casamino acid, yeast extract, pharma media, meat extract, tryptone, soytone, hypro, ajipower, soybean meal, cotton seed meal, cultivator, ajipron, zest. The inorganic nitrogen sources include ammonium sulfate, ammonium nitrate, ammonium phosphate, ammonium carbonate, sodium nitrate, ammonium acetate. Exemplary carbon sources include soluble starch, insoluble starch, amylopectin, glycogen, pullulan, and branched oligomers produced by their partial decomposition, utilizable carbon sources such as glucose, maltose, arabinose, xylose, ribose, mannose, fructose, galactose, maltose, sucrose, lactose, trehalose, mannitol, sorbitol, glycerol, utilizable organic acids such as citric acid, acetic acid, and the like. In addition to the above carbon and nitrogen sources, inorganic ions such as phosphate, magnesium, calcium, manganese, zinc, cobalt, sodium, potassium, and the like, and other organic and inorganic micronutritions substances, if necessary, can be added into the culture medium.

The target alkaline pullulanase A can be collected and purified by means of conventional collection and purification methods applied to general enzymes. Specifically, cells can be separated from the culture broth by means of conventional solid-liquid separation methods such as centrifugation, filtration or the like, to obtain a crude enzyme solution. Although it is possible to use the crude enzyme solution thus obtained as it is, it can be served as purified enzyme as required, after separated by means of separation methods such as salting out, precipitation, ultrafiltration and the like to obtain crude enzyme, further purifying and crystallizing the crude enzyme by conventional methods.

A preferable method for purifying the alkaline pullulanase A is discussed below.

Strains of an alkaline microorganism belonging to genus Bacillus KSM-AP1876 are aerobically shake-cultured in a medium containing 1% of pullulan, 0.2% of tryptone, 0.1% of yeast extract, 0.03% of $KH_2PO_4$, 0.02% of $CaCl_2.2H_2O$, 0.1% of $(NH_4)_2SO_4$, 0.001% of $FeSO_4.7H_2O$, 0.0001% of $MnCl_2.4H_2O$, 0.02% of $MgSO_4.7H_2O$ and 0.5% of sodium carbonate, at 30° C. for 3 days. Cells are removed from the culture liquid to obtain a supernatant. DEAE-cellulose powder is added to the supernatant to have pullulanase A completely adsorbed onto the DEAE-cellulose. After washing resin with 10mM tris-HCl buffer solution (pH 8), the enzyme is eluted with the same buffer solution containing 0.6M NaCl.

Further, after dialyzing and concentrating against 10 mM tris-HCl buffer solution (pH 8), the enzyme is adsorbed onto DEAE-cellulose DE52 equilibrated with the buffer solution. The enzyme is then eluted at a concentration slant of 0–1M NaCl using the mentioned buffer solution, to collect active fractions. After concentrating with an ultrafiltration membrane whose average fraction-molecular-weight is 10,000, the enzyme is dialyzed using the buffer solution containing 0.1M NaCl overnight. The obtained enzyme is concentrated and dialyzed. Then, after adsorbing onto the Sephacryl S-200 (trade-mark) column equilibrated with the said buffer solution containing 0.1M NaCl, the enzyme is eluted with the buffer solution containing 0.1M NaCl. The active fractions are collected and adsorbed onto DEAE Toyopearl 650 S (trade-mark) column. The adsorbed enzyme is eluted at a concentration slant of 0.1–1M NaCl in 10mM tris-HCl buffer solution (pH 8), and the active fractions are collected. The collected active fractions are concentrated using ultrafiltration membrane, then adsorbed to butyl Toyopearl 650S (trade-mark) column equilibrated with the said buffer solution containing 2M ammonium sulfate. The active fractions are eluted at a concentration slant of 2–0M ammonium sulfate using 10 mM tris-HCl buffer solution (pH 8), and collected. After concentrating with an ultrafiltration membrane, the active fractions are dialyzed overnight. Purified enzyme thus obtained gave a single band when subjected to electophoresis using polyacrylamide gel (gel concentration: 15%) and sodium dodecylsulfate (SDS). The active yield was about 4%.

Enzymological characteristics of the alkaline pullulanase A are described below.

Enzymatic activities were measured using the following buffer solutions (10 mM each) according to the method shown below.

| pH 4–6 | acetate buffer |
|---|---|
| pH 6–8 | phosphate buffer |
| pH 8–11 | glycine-NaCl—NaOH buffer |
| pH 11–12 | KCl—NaOH buffer |

Method for Measuring Enzymatic Activities (Pullulanase Activities)

0.1 ml of enzyme solution was added to 0.9 ml of a substrate solution consisting of a buffer solution and pullulan (final concentration in the reaction system was 0.25%), and the mixture was reacted at 40° C. for 30 minutes. After the reaction, reducing sugar was quantitatively determined by a method of the 3,5-dinitrosalicylic acid (DNS).

Specifically, 1.0 ml of DNS reagent was added to 1.0 ml of reaction mixture, and the mixture was heated at 100° C. for 5 minutes to develop color. After cooling, the mixture was diluted by adding 4.0 ml of deionized water. This solution was subjected to colorimetric quantitative analysis at a wave length of 535 nm. One unit (1U) of enzyme activity was defined as the amount of enzyme which released 1 μmol of reducing sugar (as glucose) per minute.

Enzymological Characteristics

1) Action

Decomposes α-1,6 glucoside linkage of pullulan to produce maltotriose. Hydrolyzes α-1,6 glucoside linkage of starch, amylopectin, glycogen, or their partial decomposition products.

2) Substrate specificity

Hydrolyzes a branched structure having a degree of polymerization which is not less than the degree of polymerization of maltose among sugars having a branch at α-1,6 glucoside linkage (Table 1).

TABLE 1

| Substrate | Concentration(M) | Relative activity (%) |
|---|---|---|
| Pullulan | $1 \times 10^{-5}$ | 100.0 |
| Glycogen(oyster) | $1 \times 10^{-6}$ | 0.2 |
| Glycogen(rabbit liver) | $1 \times 10^{-6}$ | 0.0 |
| Amylopectin | $1 \times 10^{-8}$ | 6.1 |
| Amylose | $1 \times 10^{-8}$ | 0.0 |
| Maltose | $1 \times 10^{-2}$ | 0.0 |
| Maltotriose | $1 \times 10^{-2}$ | 0.0 |
| Panose | $1 \times 10^{-2}$ | 0.0 |
| Isomaltose | $1 \times 10^{-2}$ | 0.0 |
| Isomaltotriose | $1 \times 10^{-2}$ | 0.0 |
| Gentiobiose | $1 \times 10^{-2}$ | 0.0 |

3) Working pH and optimum pH ranges

The working pH is in the range of 5–11 with optimum pH in the range of 9.5–11.

Pullulanase activities at various pHs were measured using reaction systems consisting of 0.25% of pullulan and each of 10 mM acetate buffer (pH 4–6), phosphate buffer (pH 6–8.5), glycine-NaCl-NaOH buffer (pH 8.5–11), and KCl-NaOH buffer (pH 11–12). Each reaction was carried out at 40° C. for 30 minutes. The results are shown in FIG. 1.

4) pH Stability

Quite stable in the pH range of 8–10, and has relative activity not less than 50% even in the pH range of 7–10.5.

Figure 2:
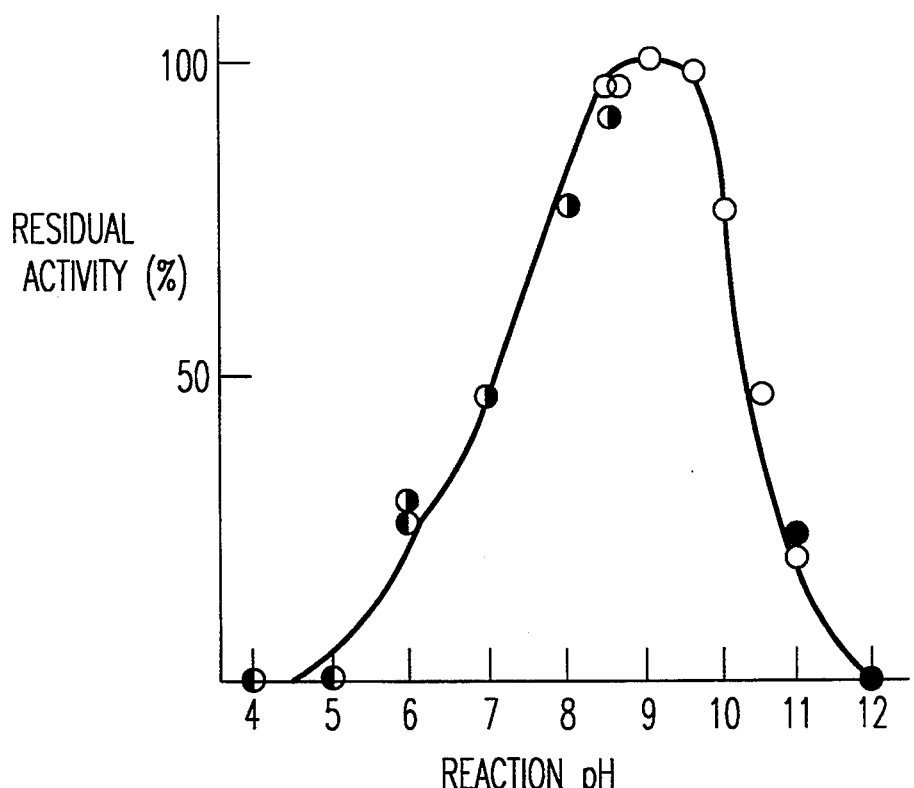
FIG. 2 shows the relation of treatment pH vs. residual activity of the alkaline pullulanase A used in the present invention.

Pullulanase activities at various pHs were measured using reaction systems consisting of 0.25% of pullulan and each of 10 mM acetate buffer (pH 4–6), phosphate buffer (pH 6–8.5), glycine-NaCl-NaOH buffer (pH 8.5–11), and KCl-NaOH buffer (pH 11–12). Each reaction was carried out at 45° C. for 10 minutes. The results are shown in FIG. 2.

5) Working temperature and optimum temperature

Figure 3:
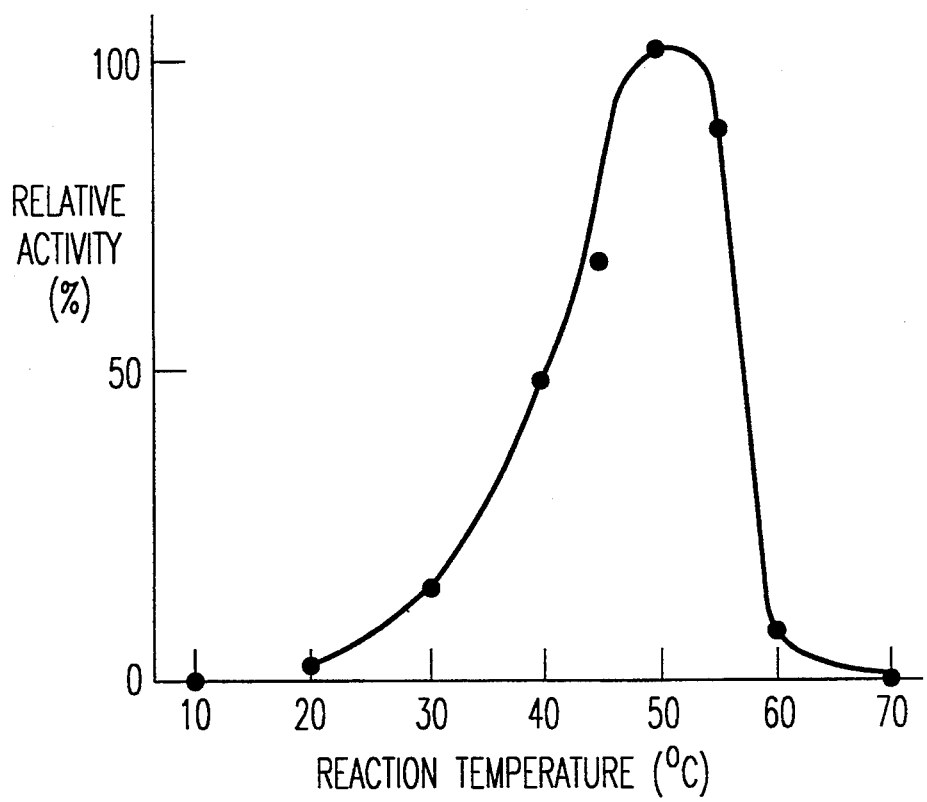
FIG. 3 shows the relation of reaction temperature (at pH 9.5) vs. relative activity of the alkaline pullulanase A used in the present invention.

Acts at wide temperature range of 10°–60° C. with an optimum temperature being about 50° C. (FIG. 3).

6) Thermal stability

Figure 4:
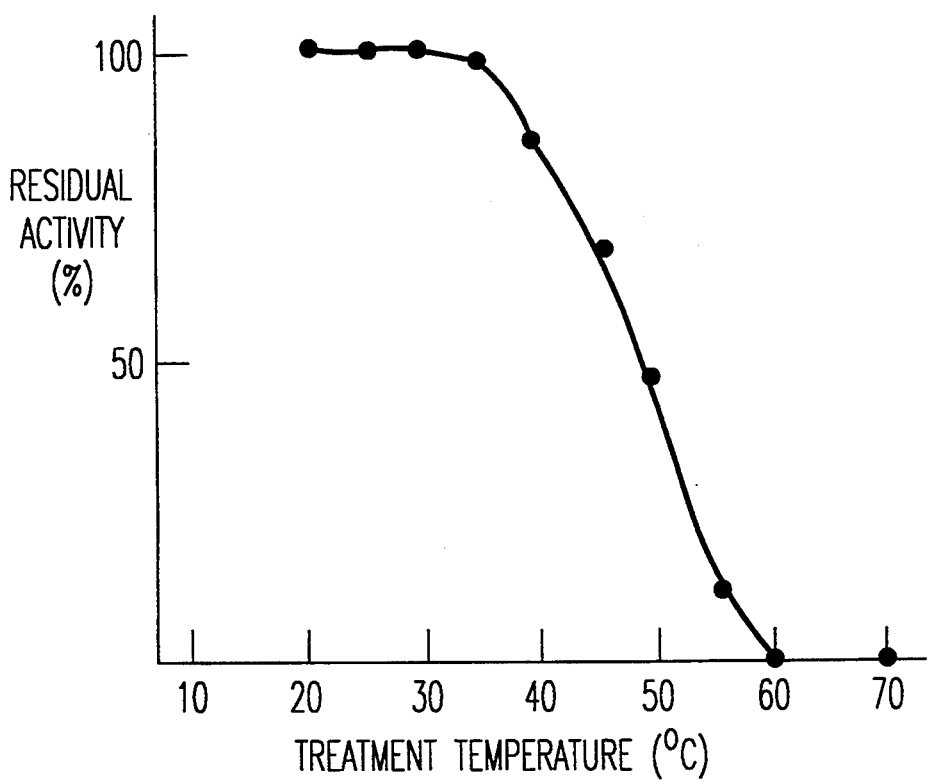
FIG. 4 shows the relation of treatment temperature (at pH 5) vs. residual activity of the alkaline pullulanase A used in the present invention.

Temperature at which the present enzyme loses its activity was examined by subjecting it to heat-treatment at various temperatures at pH 9.5 for 30 minutes. It was revealed that the enzyme was stable up to 40° C., and had residual activity of not less than 50% even at 50° C. (FIG. 4).

7) Molecular Weight

About 120,000±5,000, when measured by means of SDS electrophoresis (gel concentration: 7 5%) (FIG. 6)

8) Effects of metal ions

Pullulanase activity was adversely affected by 1 mM of $Hg^{2+}$, $Cd^{2+}$, and $Mn^{2+}$ strongly, and by 1 mM of $Pb^{2+}$ slightly.

9) Effects of surfactants

Surfactants such as linear alkylbenzene sulfonate, sodium alkyl sulfate, sodium polyoxyethylene alkyl sulfate, sodium α-olefin sulfonate, sodium α-sulfonated fatty acid ester, sodium alkyl sulfonate, sodium dodecyl sulfate, soaps, and Softanol (trade-mark) gave almost no adverse effects when the enzyme was treated with 0.05% solution of each of the surfactants at 40° C. for 15 minutes.

10) Effects of chelating agents

Chelating agents such as EDTA (10 mM), EGTA (10 mM), citric acid (0.05% by weight) gave almost no adverse effects on pullulanase activity.

11) Resistance to protease

The enzyme exhibited strong resistance to any alkaline proteases such as API-21 (manufactured by Showa Denko Co.), Maxatase (manufactured by IBIS Co.), Sabinase (manufactured by Novo Co.), Alkalase (by Novo Co.), Espelase (by Novo Co.) or the like, when measured in their presence (0.2 AU/1).

On the other hand, as for the alkaline pullulanase B usable in the present invention, alkaline pullulanase which is produced, for example, by an alkalophilic microroganism such as Bacillus sp KSM-AP 1378 (FERM BP-3048) shown below is mentioned.

This microorganism has the following mycological characteristics.

Mycological Characteristics a) Observation under microscope

Cells are rods of a size of 0.8–2.4 μm×1.8–4.0 μm, with an elliptical endospore (1.0–1.2 μm×1.2–1.4 μm) forming at their subterminals. They have flagella and are motile. Gram's strain is indefinite. Acid fastness is negative.

b) Growth in various culture media

1) Broth agar plate culture (Medium 1)

Growth of cells is good. Colony has a circular shape, with its surface being smooth and its peripheral being smooth. The color of the colony is yellow, semitransparent, and glossy.

2) Broth agar slant culture (Medium 1)

Cells can grow. Colony has a cloth-spreading shape, with color of the colony being glossy, yellow, and semi-transparent.

3) Broth liquid culture (Medium 2)

Cells can grow

4) Stab culture in broth-gelatin (Medium 3)

Growth of cells is good. Liquefaction of gelatin is observed.

5) Litmuth milk medium (Medium 4)

Milk coagulation and peptonization are not observed. Litmuth discoloration is indeterminable because the medium is an alkaline medium.

c) Physiological characteristics

1) Nitrate reduction and denitrification (Medium 5)

Nitrate reduction is positive. Denitrification is negative.

2) MR test (Medium 6)

Indeterminable because the medium is an alkaline medium.

3) VP test (Medium 6)

Negative.

4) Production of indole (Medium 7)

Negative.

5) Production of hydrogen sulfide (Medium 8)

Negative.

6) Hydrolysis of starch (Medium 9)

Positive

7) Utilization of citric acid

Negative in Koser's medium (Medium 10), and indeterminable in Christensen's medium (Medium 11).

8) Utilization of inorganic nitrogen sources (Medium 12)

Nitrate, ammonium salts, and nitrite are all utilized.

9) Discoloration (Medium 13, Medium 14)

Negative.

10) Urease (Medium 15)

Negative.

11) Oxidase (Medium 16)

Negative

12) Catalase (Medium 17)

Positive

13) Growth range (Medium 18)

Growth temperature : 20°–40° C. Optimum growth temperature: 30°–35° C. Growth pH range: 7–10.5 Optimum growth pH: 10

14) Behavior towards oxygen

Aerobic.

15) O-F test (Medium 19)

Discoloration is indeterminable because the medium is an alkaline medium. Cells can grow only under aerobic conditions.

16) Sugar utilization (Medium 20)

L-Arabinose, D-xylose, D-glucose, D-mannose, D-fructose, D-galactose, maltose, sucrose, lactose, trehalose, D-sorbitol, D-mannitol, inositol, glycerol, starch, raffinose, salicin, D-ribose, and dextrin are utilized.

17) Growth in a medium containing sodium salt (modification of Medium 1)

Cells can grow in the presence of 7% NaCl but cannot prow in the presence of 10% NaCl 18) Hydrolysis of casein (Medium 21)

Positive.

Based on the above mycological characteristics, the strain of the present invention was examined referring to Bergey's Mannual of Determinative Bacteriology, 8th ed., and 'The Genus Bacillus' Ruth, E. Gordon, Agriculture Handbook No. 427, Agricultural Research Service, U.S. Department of Agriculture, Washington D.C. (1973), and determined as an asporogenas rod-shaped microorganism belonging to the genus Bacillus. The strain did not grow in a neutral pH range, but grew mostly in a highly alkaline range. From this fact, the strain of the present invention was classified as an alkalophilic microorganism which was demonstrated by Horikoshi and Akiba [Alkalophilic Microorganisms, Japan Scientific Society Press (Tokyo), 1982]. The strain of the present invention is distinguished from a group of microorganisms belonging to the genus Bacillus which grows in a neutral pH range The strain of the present invention has mycologically different characteristics from those of any conventionally known 'alkanophilic Bacillus'. Accordingly, the strain of the present invention was determined as a novel strain, and named Bacillus sp. KSM-AP 1378, which was deposited with Fermentation Research Institute, Agency of Industrial Science and Technology as FERM BP-3048.

The production of the alkaline pullulanase B used in the present invention can be processed by inoculating the above microorganisms according to the conventional cultivating methods. It is desirable to add a suitable amount of carbon and nitrogen sources which the microorganism can utilize in the medium. There are no specific limitations as to carbon and nitrogen sources.

Exemplary nitrogen sources include corn gluten meal, soybean flour, corn steep liquor, casamino acid, yeast extract, pharma media, meat extract, tryptone, soytone, hypro, ajipower, cotton seed meal, cultivator, ajipron and zest. The inorganic nitrogen sources include ammonium sulfate, ammonium nitrate, ammonium phosphate, ammonium carbonate, sodium nitrate, ammonium acetate and the like. Exemplary carbon sources include soluble starch, insoluble starch, amylopectin, glycogen, pullulan and branched oligomers produced by their partial decomposition, and utilizable carbon sources such as glucose, maltose, arabinose, xylose, ribose, mannose, fructose, galactose, sucrose, lactose, trehalose, mannitol, sorbitol, glycerol, and utilizable organic acids such as citric acid, acetic acid and the like. In addition to the above carbon and nitrogen sources, inorganic ions such as phosphate, magnesium, calcium, manganese, zinc, cobalt, sodium, potassium and the like, and other organic or inorganic micronutritious substances, if necessary, can be added into the culture medium.

A preferable culturing temperature is from 20° to 40° C., most preferably from 30° to 35° C., and pH is from 8 to 10.5, preferably 10. The cultivation is usually completed in 2-3 days under the above conditions.

The target alkaline pullulanase B having α-amylase activity can be collected and purified by means of conventional collection and purification methods applied to general enzymes. Specifically, cells can be separated from the culture broth by means of conventional solid-liquid separation methods such as centrifugation, filtration or the like, to obtain a crude enzyme solution.

Although it is possible to use the crude enzyme solution thus obtained as it is, it can be served as purified enzyme, after separated by means of separation methods such as salting out, precipitation, ultrafiltration and the like to obtain a crude enzyme, further purifying and crystalyzing the crude enzyme by conventional methods, as required.

A preferable method for purifying alkaline pullulanase B is discussed below.

Strains of an alkaline microorganism belonging to genus Bacillus KSM-AP 1378 are aerobically shake-cultured in a medium containing 1% of pullulan, 1% polypeptone, 0.5% of yeast extract, 0.1% of $KH_2PO_4$, 0.25% of $Na_2HPO_4.12H_2O$, 0.02% of $MgSO_4.7H_2O$ and 0.5% of sodium carbonate, at 30° C. for 3 days. Cells are removed from the culture broth to obtain a supernatant. The supernatant is then purified by means of DEAE cellulose adsorption, α-cylodextrin affinity chromatography, DEAE Toyopearl (manufactured by Toyo Soda Co.) chromatography, and Sephacryl (manufactured by Pharmacia Co.) chromatography. Purified enzyme thus obtained gave a single band when it is subjected to electophoreses using polyacrylamide gel (gel concentration: 15%) or sodium dodecyl sulfate (SDS). In this process, the active yield was about 2%.

Alkaline pullulanase B thus obtained is preferably used as an component of the detergent composition of the present invention. Enzymological characteristics of alkaline pullulanase B are explained below.

Enzymatic activities were measured using the following buffer solutions (50 mM each) according to the method explained below.

| pH 4–6: | acetate buffer |
| pH 6–8: | phosphate buffer |
| | (for measuring pullulanase activity) |
| pH 6–8: | Tris-malate buffer |
| | (for measuring α-amylase activity) |
| pH 8–11: | glycine-NaCl—NaOH buffer |
| pH 11–12: | KCl—NaOH buffer |

Method for Measuring Enzymatic Activities

1) Pullulanase activity

Same procedures were followed as mentioned in the section of alkaline pullulanase A.

2) α-amylase activity 0.1 ml of enzyme solution was added to 0.9 ml of a substrate solution consisting of a buffer solution and soluble starch (final concentration in the reaction system was 0.25%), and the mixture was reacted at 50° C. for 15 minutes. After the reaction, reducing sugar was quantitatively determined by means of a DNS method. Specifically, 1.0 ml of DNS reagent was added to 1.0 ml of reaction mixture, and the mixture was heated at 100° C. for 5 minutes to develop color. After cooling, the mixture was diluted by adding 4.0 ml of deionized water. This solution was subjected to colorimetric quantitative analysis at wave length of 535 nm. One unit (1U) of enzyme activity was defined as the amount of enzyme which released 1 μmol of reducing sugar (as glucose) per minute.

Enzymological Characteristics

1) Action

Figure 7:
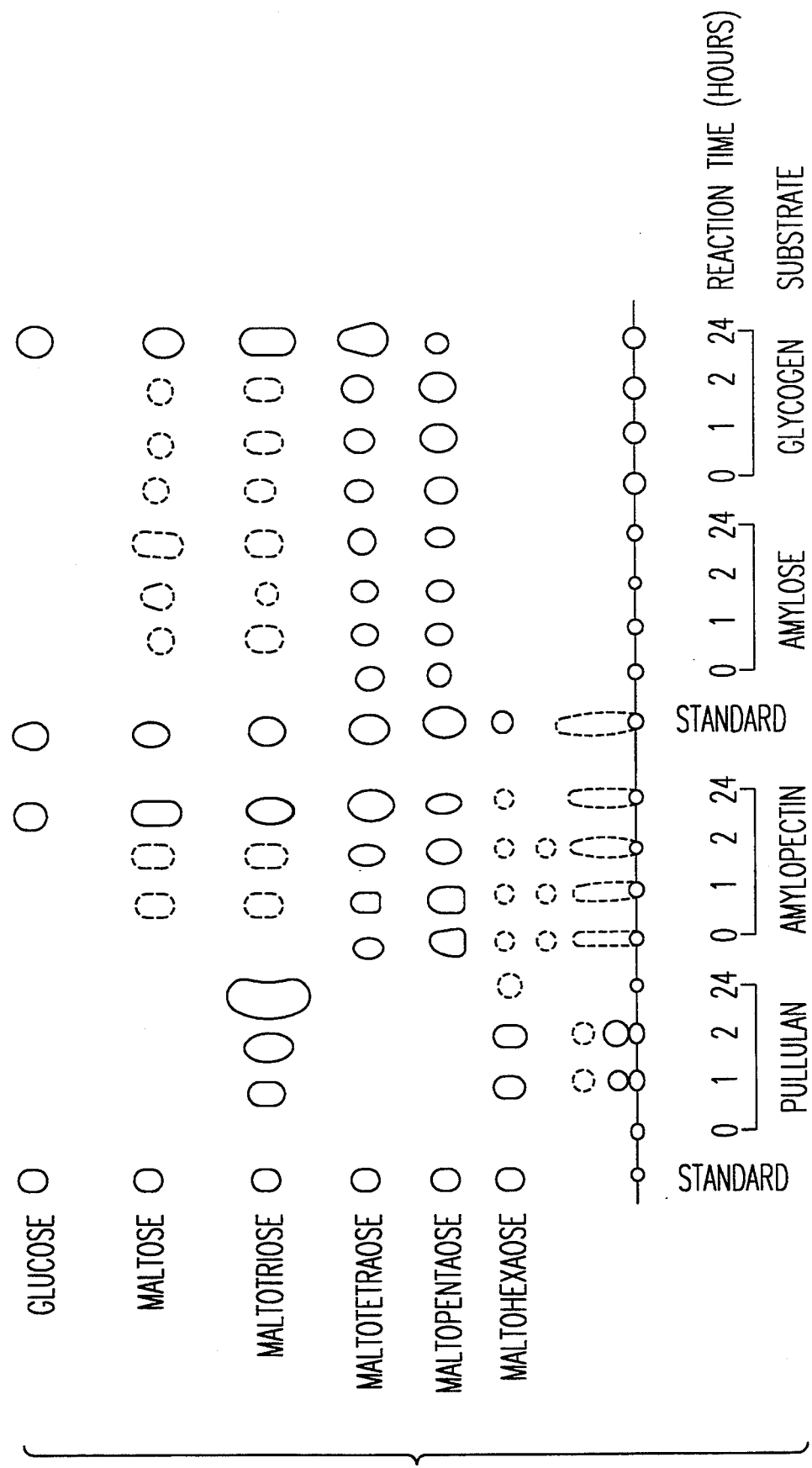
FIG. 7 is a paper chromatography profile showing the production of maltooligosaccharides from the enzymatic reaction between the alkaline pullulanase B having an α-amylase activity, and several substrates (pullulan, amylopectin, amylose, and glycogen).

Acts on pullulan and soluble starch to produce mainly maltotriose from pullulan and mainly maltotetraose and maltopentaose from soluble starch. Acts also on glycogen to produce maltotetraose and maltopentaose (FIG. 7).

2) Substrate specificity

Acts on pullulan, soluble starch, and glycogen (Table 2).

TABLE 2

| Substrate | Concentration | Relative activity (%) |
| --- | --- | --- |
| Pullulan | 0.25% | 100 |
| Glycogen (oyster) | 0.5% | 25 |
| Glycogen (rabbit liver) | 0.5% | 24 |
| Amylopectin | 0.5% | 55 |
| Amylose | 0.5% | 28 |
| Maltose | $1 \times 10^{-2}M$ | 0 |
| Maltotriose | $1 \times 10^{-2}M$ | 0 |
| Panose | $1 \times 10^{-2}M$ | 0 |
| Isomaltose | $1 \times 10^{-2}M$ | 4 |
| Isomaltotriose | $1 \times 10^{-2}M$ | 11 |
| Gentiobiose | $1 \times 10^{-2}M$ | 0 |

3) Working pH and optimum pH ranges

The working pH on pullulan of alkaline pullulanase B is in the range of 5–12 with an optimum pH in the range of 8.5–10.

Figure 8A:
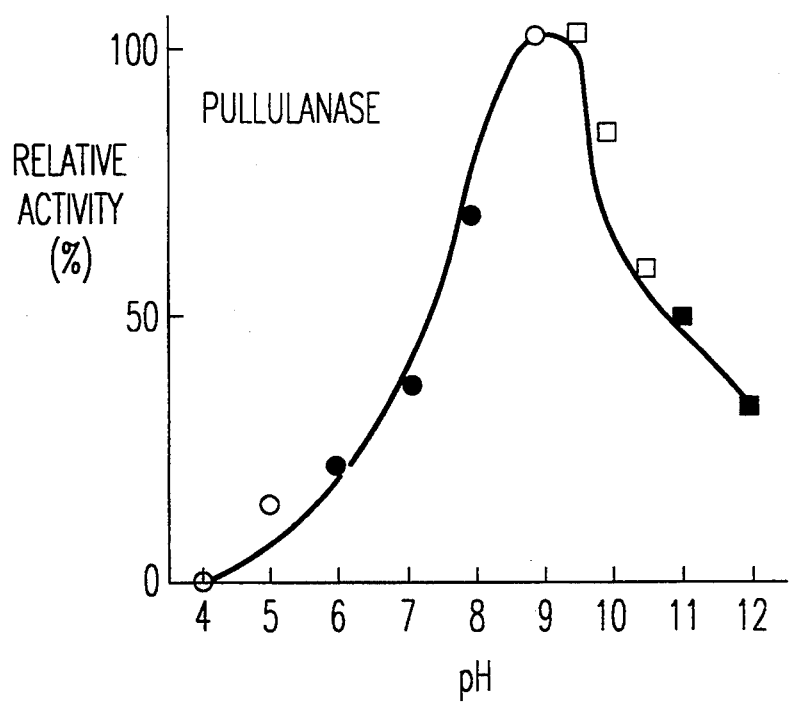
FIGS. 8(a) and 8(b) show the relation of reaction pH vs. relative activity of the alkaline pullulanase B having α-amylase activity used in the present invention.

Pullulanase activities at various pHs were measured using reaction systems consisting of 0 25% of pullulan and each of 10 mM acetate buffer (pH 4–5), phosphate buffer (pH 6–8), glycine-NaCl-NaOH buffer (pH 9–10.5), and KCl-NaOH buffer (pH 11–12). Each reaction was carried out at 40° C. for 30 minutes. The results are shown in FIG. 8(a).

Figure 8B:
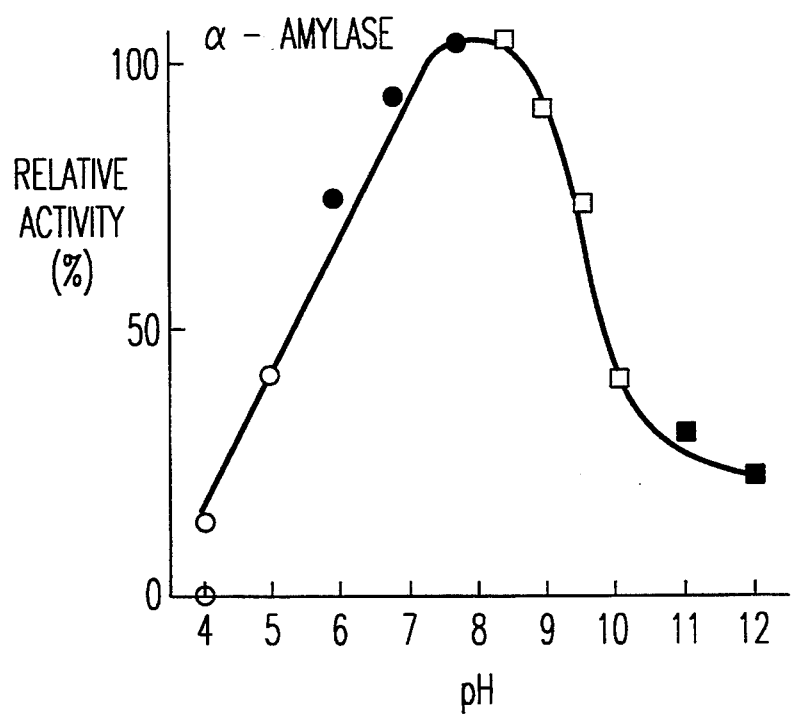

The working pH on soluble starch was in the range of 4–12 with an optimum pH in the range of 7–9.5. α-Amylase activities at various pHs were measured using reaction systems consisting of 0.25% of soluble starch and each of 10 mM acetate buffer (pH 4–5), tris-malate buffer (pH 6–8), glycine-NaCl-NaOH buffer (pH 9–10.5), and KCl-NaOH buffer (pH 11–12). Each reaction was carried out at 50° C. for 15 minutes. The results are shown in FIG. 8(b).

4) pH stability

Figure 9A:
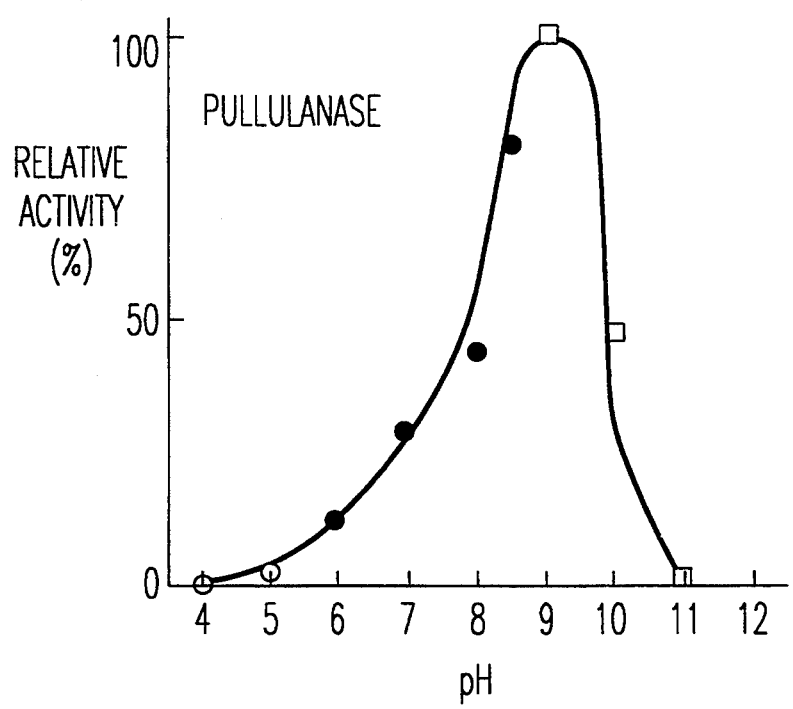
FIGS. 9(a) and 9(b) show the relation of treatment pH vs. residual activity of the alkaline pullulanase B having α-amylase activity used in the present invention.

Alkaline pullulanase B is stable in the pH range of 6–10.5 against pullulan. Pullulanase activities at various pHs were measured using reaction systems consisting of 0.25% of pullulan and each of 10 mM acetate buffer (pH 4–5), phosphate buffer (pH 6–8), glycine-NaCl-NaOH buffer (pH 9–10.5), and KCl-NaOH buffer (pH 11–12). Each reaction was carried out at 45° C. for 10 minutes. The results are shown in FIG. 9(a).

Figure 9B:
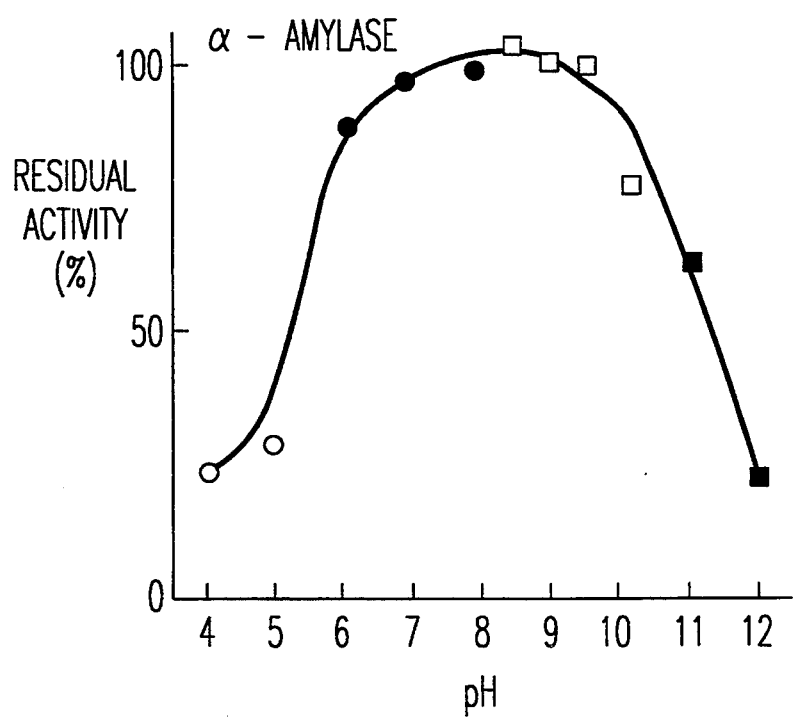

Alkaline pullulanase B of this invention was stable in the pH range of 4–12 against soluble starch. α-Amylase activities at various pHs were measured using reaction systems consisting of 0.25% of pullulan and each of 10 mM acetate buffer (pH 4–5), tris-malate buffer (pH 6–8), glycine-NaCl-NaOH buffer (pH 9–10.5), and carbonate buffer (pH 11–12). Each reaction was carried out at 50° C. for 15 minutes. The results are shown in FIG. 9(b).

5) Working temperature and optimum temperature

Figure 10A:
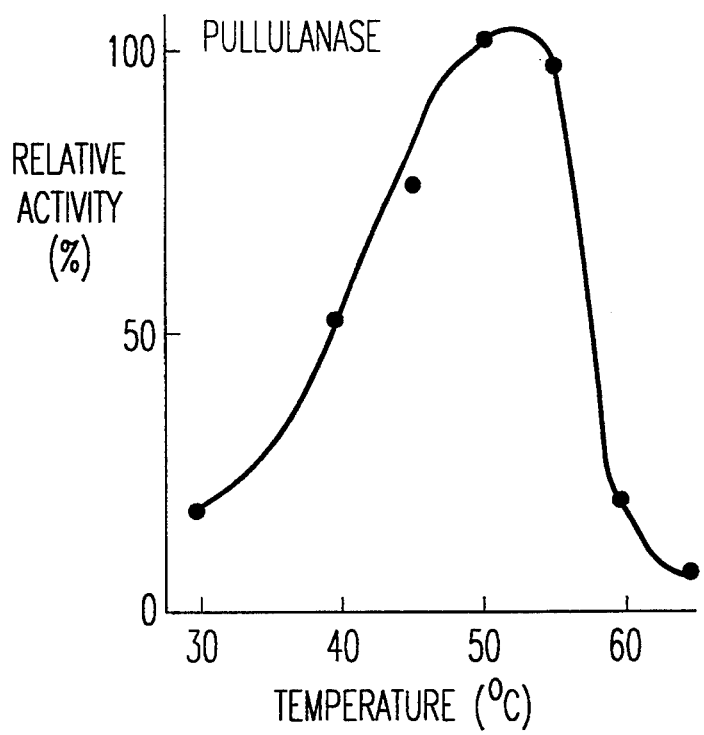
FIGS. 10(a) and 10(b) show the relation of reaction temperature (at pH 9.5) vs. relative activity of the alkaline pullulanase B having α-amylase activity used in the present invention.
Figure 10B:
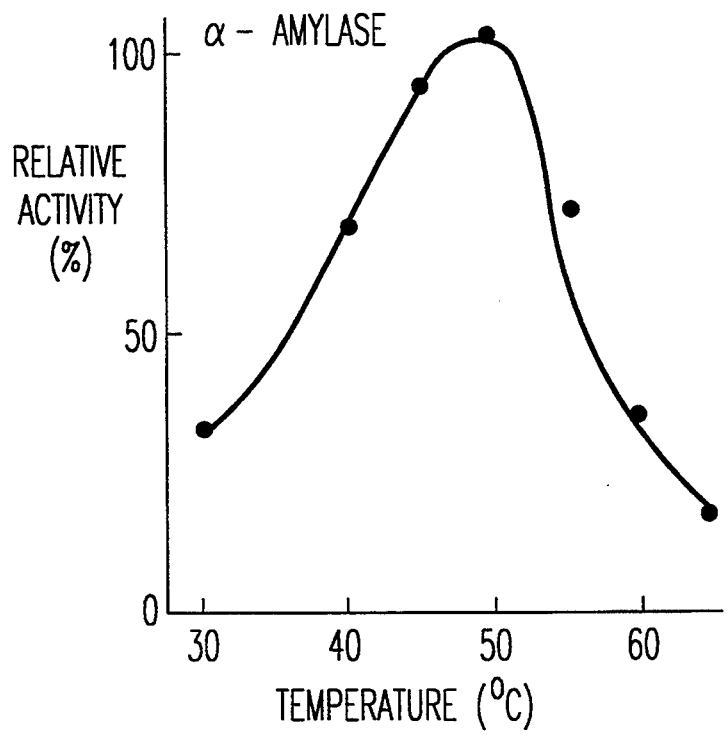

Acts on pullulan and soluble starch at a wide temperature range of 10°–65° C. with an optimum temperature being about 50° C. The results are shown in FIGS. 10(a) and 10(b).

Thermal stability

Figure 11A:
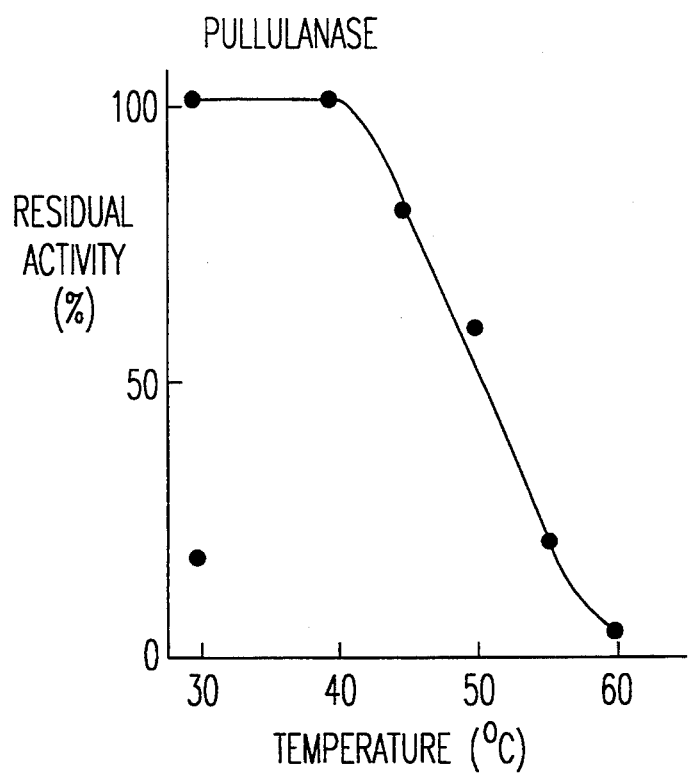
FIGS. 11(a) and 11(b) show the relation of treatment temperature (at pH 9.5) vs. residual activity of the alkaline pullulanase B used in the present invention.
Figure 11B:
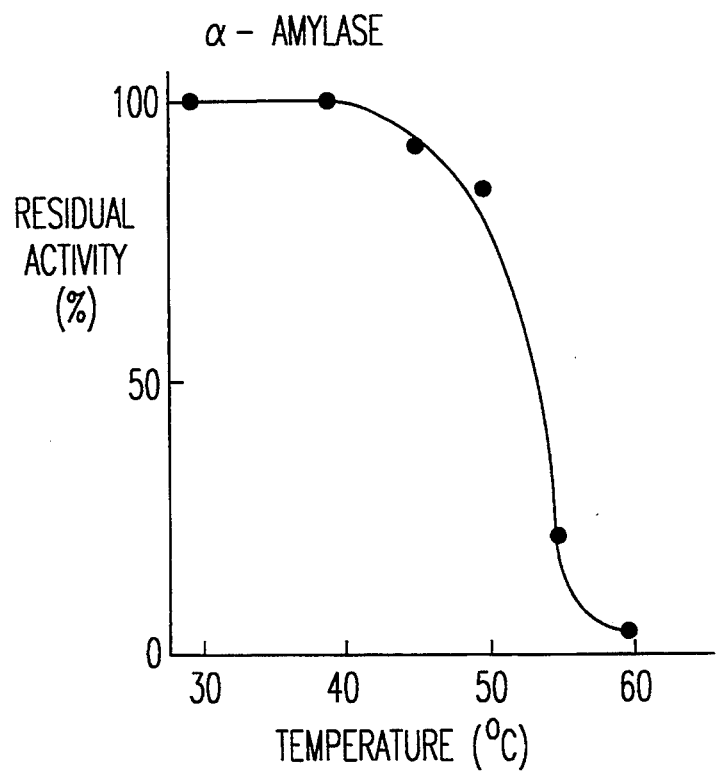

Temperature at which the present enzyme loses its activity was examined by subjecting it to heat-treatment at various temperatures at pH 9.5 for 30 minutes. As a result, the enzyme was very stable tip to 45° C. The results are shown in FIGS. 11(a) and (b).

7) Molecular weight

Figure 13:
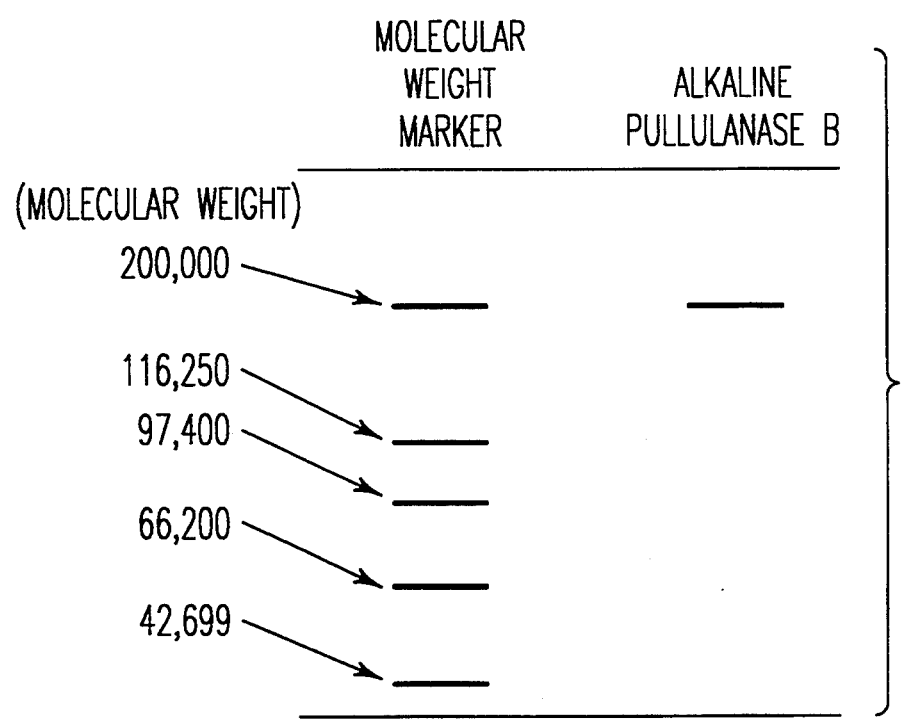

About 200,000±5,000, when measured by means of SDS electrophoresis (gel concentration: 7.5%). (FIG. 13)

8) Effects of metal ions

Pullulanase activity was adversely affected by $Hg^{2+}$, $Mn^{2+}$, and $Pb^{2+}$ ions, and α-amylase activity was adversely affected by $Hg^{2+}$, $Mn^{2+}$, $Pb^{2+}$, $Cd^{2+}$, and $Zn^{2+}$. The results are shown in Table 3.

TABLE 3

| Compound | Concentration | Residual activity (%) Pullulanase activity | Residual activity (%) α-Amylase activity |
|---|---|---|---|
| No addition | — | 100 | 100 |
| Metal salt | | | |
| $HgCl_2$ | 1 mM | 36 | 53 |
| $MnCl_2$ | 1 mM | 51 | 28 |
| $PbCl_2$ | 1 mM | 53 | 53 |
| $CdCl_2$ | 1 mM | 80 | 38 |
| $ZnCl_2$ | 1 mM | 93 | 57 |
| Chlating agent | | | |

TABLE 3-continued

| Compound | Concentration | Residual activity (%) Pullulanase activity | Residual activity (%) α-Amylase activity |
|---|---|---|---|
| EDTA | 10 mM | 77 | 17 (88)* |
| EGTA | 10 mM | 65 | 18 (91)* |

*: The values in parentheses are residual activities when $Ca^{2+}$ ions were added again.

As shown in Table 3, the metal ions which adversely affect the pullulanase activity and those which adversely affect the α-amylase activity are discriminated from each other.

9) Effects of surfactants 0.05% Solution of surfactants such as linear alkylbenzene sulfonate, sodium polyoxyethylene alkylsulfate, sodium α-olefin sulfonate, sodium α-sulfonated fatty acid ester, sodium alkyl sulfonate, sodium dodecyl sulfate, soaps, and softanol were tested at 40° C. for 15 minutes to give almost no adverse effect on enzyme activies.

10) Effects of chelating agents Chelating agents such as EDTA (10 mM), EGTA (10 mM) gave almost no adverse effect on pullulanase activity. But α-amylase activity was adversely affected significantly. The α-amylase activity which had been adversely affected by chelating agents can be restored by the addition of $Ca^{2+}$ ions as shown in Table 3.

11) Resistance to protease

In the presence of an alkaline protease, for example, Maxatase (manufactured by IBIS Co.), Sabinase (manufactured by Novo Co.) or the like in an amount of 0.2 AU/l, the activities were measured, to confirm that the enzyme of this invention exhibited strong resistance to any proteases.

As is apparent from the above-mentioned enzymological characteristics, the alkaline pullulanase B of the present invention is the one having different physiological and chemical characteristics from conventional pullulanases having α-amylase activity.

Further, in order to clarify the novelty of the enzyme of the present invention, comparison data on physiological and chemical characteristics of the enzyme of the present invention and conventional pullulanases having α-amylase activity are shown in Table 4.

As is apparent from Table 4, the alkaline pullulanase B of the present invention is clearly different from a pullulanase-amylase complex derived from Bacillus subtitis TU or from an amylase having pullulanase activity derived from Bacillus circulans F-2.

TABLE 4

| | Pullulanase | | |
|---|---|---|---|
| | Japanese Patent Publication (Kokoku) No. 18717/1989 | Japanese Patent Laid-open (Kokai) No. 60376/1989 | Present Invention (Alkaline Pullulanase B) |
| Microorganism | Bacillus subtilis Tu | Bacillus circulans F-2 | Bacillus sp. KSM-AP 1378 |
| Optimum pH of pullulanase activity | 7.0–7.5 | 7.0 | 8.5–10.0 |
| Optimum pH of α-amylase activity | 6.7–7.0 | 7.0–8.5 | 7.0–9.5 |
| Optimum temperature of pullulanase activity | 50° C. | 50° C. | 50–55° C. |
| Optimum temperature of α-amylase activity | 60° C. | 50° C. | 45–50° C. |
| Molecular weight | 450,000 (gel filtration) | 218,000 (SDS electrophoresis) | 200,000 (SDS electrophoresis) |

TABLE 4-continued

| | Pullulanase | | |
|---|---|---|---|
| | Japanese Patent Publication (Kokoku) No. 18717/1989 | Japanese Patent Laid-open (Kokai) No. 60376/1989 | Present Invention (Alkaline Pullulanase B) |
| Major products from soluble starch* | G1, G2, G3 | G4, G5, G6 | G4, G5 |
| Major products from pullulan* | G3 | G3 | G3 |

*: G1: glucose, G2: maltose, G3: maltotriose, G4: maltotetraose, G5: maltopentaose, G6: maltohexaose The above-mentioned alkaline pullulanase A or alkaline pullulanase B are generally incorporated into a detergent composition of the present invention by 0.1–10 wt. %. These alkaline pullulanases can be used either in the purified form of enzyme, or as an crude enzyme which is culture broth itself.

Other conventional detergent components may optionally be compounded into the detergent composition of the present invention depending on the use and the purposes. These components to be compounded are illustrated below. 1) The amount of surfactants is not limited especially, but is preferably 0.5–60% by weight. The exemplary surfactants usable for the detergent comosition of the present invention include nonionic surfactants such as alkylbenzene sulfonate, alkyl or alkenylether sulfate, alkyl or alkenyl sulfate, olefin sulfonate, alkane sulfonate, saturated or unsaturated fatty acid salt, alkyl or alkenyl ether carboxylic acid salt, α-sulfo fatty acid salt or ester, aminoacid-type surfactant, N-acylamino acid-type surfactant, alkyl or alkenyl acid-phosphate, alkyl or alkenyl phosphate or its salt; amphoteric surfactants such as carboxyl or sulfobetaine-type surfactant; nonionic surfactants such as polyoxyalkylene alkyl or alkenyl ether, polyoxyethylene alkyl phenyl ether, higher fatty acid alkanolamide or its alkylene oxide adduct, sucrose fatty acid ester, fatty acid glycerol monoester, alkylamine oxide, alkylglycoside; and cationic surfactants such as quaternary ammonium salt.

When the detergent composition of this invention is used for automatic dish-washing, little- or non-foaming nonionic surfactants are preferable. As for these kinds of surfactants, alkoxylated nonionic surfactants (alkoxyl moiety is selected from the group consisting of ethylene oxide, propylene oxide and their mixtures) are enumerated. Mention may be given to 'Plurafac LF 403' and 'Plurafac LF 1300' (both trade-marks, manufactured by BASF Japan Co.), 'Softanol EP 7045' (trade-mark, manufactured by Nippon Shokubai Kagaku Kogyo K.K.). When the detergent composition is used for an automatic dish-washer, it is preferable that the surfactants of 0.5%–30% by weight are compounded into the composition.

2) Alkaline agents such as carbonate, hydrogencarbonate, silicate, boronate and alkanolamine and inorganic electrolytes such as sulfate are usually compounded into the composition in an amount of 0–90% by weight.

3) Phosphates such as tri-poly phosphate, pyrophosphate, orthophosphate; phosphonates such as ethane-1, 1-diphosphonate; phosphono carboxylates such as 2-phosphonobutane-1,2-dicarboxylate; amino acid salts such as aspartate, glutamate; aminopolyacetates such as nitrilo triacetate, ethylenediamine tetraacetate; polymer-chelating agents such as polyacrylate, polyakonitate; organic acid salts such as oxalate, citrate; divalent metal ion scavengers such as alumino silicate are usually compounded into the composition in an amount of 0–50% by weight.

4) Bleaching agents such as sodium percabonate, sodium perboronate, sodium hypochloride, dichloro isosialic acid are compounded into the composition in an amount of 0–85% by weight.

5) As for the other small quantity components which may be incorporated as required, mention may be given to anti-recontamination agents such as polyethylene glycol, carboxy methyl cellulose; enzymes such as protease, lipase, α-amylase, cellulase; anti-enzyme quenchers such as sulfite; fluorescent dyes; blueing agents; colorants; anti-caking agents; solubilizing agents; activating agents for enzymes or bleaching agents; anti-metal-corrosion agents.

Exemplary proteases to be used in the present invention include subtilicins obtained from specific strains such as Bacillus subtilis and Bacillus licheniformis. For example, 'Maxatase' (trade-mark, Gist- Brocades), 'Alkalase', 'Esperase' and 'Sabinase' (trademarks, Novo Industry Co.), are enumerated.

α-Amylase to be used in the present invention are obtained, for example, from Bacillus licheniformis or Bacillus subtilis. Commercially available examples are 'Termamyl' (trade-mark, Novo Industry Co.), 'Maxamyl' (trade-mark, Gist-Brocades).

When the detergent composition is used for an automatic dish-washer of power or granule forms, inorganic alkaline agents are preferably used as the balance components. Such inorganic alkaline agents include sodium pyrolate, sodium orthophosphate, sodium tripolyphosphate, sodium carbonate, sodium hydrogencarbonate, sodium sesquicarbonate, borax, sodium silicate and the like. Since sodium silicate works as an anti-metal-corrosion agent, it is desirable to use it together with other alkaline agents. It is the most desirable that the sodium silicate ($SiO_2/Na_2O = 1/1-4/1$, preferably $2/1-2.5/1$) (concentration: 2–15% by weight) and the other alkaline agents (concentration: 35–85% by weight) are used together. The amount of the inorganic alkaline agents are controled so that the pH of a detergent solution (concentration: 0.05–1% by weight) falls in the range of is 9.0–11.0. When the detergent composition is liquid, balance component is water.

Fatty acids, hydrocarbon-chain-length of which is in a degree of 8–18, benzotriazole and the like are effectively added to the detergent composition for an automatic dishwasher as an anti-copper-corrosion agent.

Recently, environmental problems caused from phosphate-containing detergents has become a controvercial subject. Accordingly, it is important that the detergents should contain no phosphor while maintaining good detergency against various kinds of contamination.

When removing phosphor, hydroxy polyhydric carboxyl acids or their water soluble salts of formula (I) are preferably used as divalent metal ion scavengers.

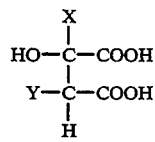

wherein X represents —H, —CH$_3$, —CH$_2$COOH or —CH(OH)COOH and Y represents —H or —OH.

Among the above compounds, citric acid, malic acid, tartaric acid or their water soluble salts are preferably used. As for the salts, salts of sodium, potassium, monoethanolamine, diethanolamine, triethanolamine and the like are mentioned.

Such components are preferably compounded into the detergent composition of the present invention in an amount of 0.5–30% by weight.

Further, polymer chelating agents in an amount of 1–10% by weight are preferably used as divalent-metal scavengers. The illustrative polymer chelating agents include those described Japanese Patent Application Laid-open (Kokai) No. 145199/1982, and polymers of acrylic or methacrylic acid, acrylic acid-methacrylic acid copolymer, their water soluble salts and the like. Their average molecular weight is 1,500–100,000, preferably 8,000–20,000.

The detergent compositions of the present invention are suitably used as detergents for clothings, dishes, households and the like in the form of powder, granule, or liquid, by blending the above-mentioned components according to conventional methods.

Other features of the invention with become apparent in the course of the following description of the exemplary embodiments which are given for illustration of the invention and are not intended to limit thereof.

EXAMPLES

Preparation Example 1

A spoonful of soil (about 0.5 g) of Yokohama-city, Kanagawa-prefecture, Japan was suspended in sterilized saline, and the mixture was heat-treated at 80° C. for minutes. Supernatant of the heat-treated mixture was appropriately diluted, and applied onto an agar medium (Medium A) for separating, then cultivating at 30° C. for 3 days to grow colonies. The colonies which formed transparent zones in their peripheries due to pullulan dissolution were collected to obtain strains which produce pullulanase A. Further, these strains were inoculated into the liquid medium (Medium B), and shake-caltivated at 30° C. for 3 days.

After the cultivation, the culture broth was centrifuged to separate a supernatant. The pullulanase activities were measured at pH 10 to select strains which produce alkaline pululanase A. Bacillus sp. KSM-AP 1876 (FERM BP-3049) which is a microorganism capable of producing alkaline pullulanase A was thus obtained.

| Medium A | Pullulan | 0.8% |
|---|---|---|
| | Colored pullulan | 0.2 |
| | Polypeptone | 0.2 |
| | Yeast extract | 0.1 |
| | KH$_2$PO$_4$ | 0.03 |
| | (NH$_4$)$_2$SO$_4$ | 0.1 |

| | | -continued |
|---|---|---|
| | MgSO$_4$.7H$_2$O | 0.02 |
| | CaCl$_2$.2H$_2$O | 0.02 |
| | FeSO$_4$.7H$_2$O | 0.001 |
| | MnCl$_2$.4H$_2$O | 0.0001 |
| | Agar | 1.5 |
| | Na$_2$CO$_3$ | 0.5 |
| | pH 10.0 | |
| Medium B | Pullulan | 1.0% |
| | Tryptone | 0.2 |
| | Yeast extract | 0.1 |
| | KH$_2$PO$_4$ | 0.03 |
| | (NH$_4$)$_2$SO$_4$ | 0.1 |
| | MgSO$_4$.7H$_2$O | 0.02 |
| | CaCl$_2$.2H$_2$O | 0.02 |
| | FeSO$_4$.7H$_2$O | 0.001 |
| | MnCl$_2$.4H$_2$O | 0.0001 |
| | Na$_2$CO$_3$ | 0.5 |
| | pH 10.0 | |

2) The strains of Bacillus sp. KSM-AP 1876 which produce alkaline pullulanase A were inoculated into the liquid Medium B, and shake-cultivated at 30° C. for 3 days. After the cultivation, cells were removed by means of centrifugation to obtain a crude pullulanase solution. The solution was processed according to a conventional method to prepare ethanol-dried powder. The crude enzyme samples shown in Table 5 were obtained. Enzymatic activities were measured at pH 9.

TABLE 5

| Strain | Amount of crude enzyme per 1 l of medium (g) | Enzyme activity (U/g) |
|---|---|---|
| KSM-AP 1876 | 0.2 | 1870 |

3) The crude enzyme solution prepared in 2) was treated by the following steps 1–5.
1. DEAE—cellulose adsorption
2. DEAE—cellulose (manufactured by Wattman Co.) Chromatography
3. Sephacryl (manufactured by Pharmacia Co.) Chromatography
4. DEAE Toyopearl (manufactured by Toyo Soda Co.) Chromatography
5. Butyl Toyopearl (manufactured by Toyo Soda Co.) Chromatography The crude enzyme was thus purified to obtain alkaline pullulanase A.

The alkaline pullulanase A obtained was subjected to electrophoresis according to the method of Davis [Davis D. J., Ann. N.Y. Acad. Sci., 121, 404, (1964)], and stained with Coomassie brilliant Blue to confirm that it gave a single band (FIG. 5).

4) The alkaline pullulanase A obtained in 3) was subjected to sodium dodecyl sulfate (SDS) electrophoresis according to a conventional method to confirm that the enzyme had a molecular weight of 120,000±5,000.

Preparation Example 2

A spoonful of soil (about 0.5 g) of Tochigi-city, Tochigi-prefecture, Japan was suspended in sterilized saline, and the mixture was heat-treated at 80° C. for 15 minutes. Supernatant of the heat-treated mixture was appropriately diluted, and applied onto an agar medium (Medium C) for separation, then cultivated at 30° C. for 3 days to grow colonies. The colonies which formed transparent zone in their peripheries due to dissolution of colored pullulan and colored starch were collected to obtain strains which produce pullulanase B. Further, these strains were inoculated into the liquid medium (Medium and shake-cultivated at 30° C. for 3 days. After the cultivation, the culture broth was centrifuged to separate a supernatant. The pullulanase activities were measured at pH 10 to select strains which produce alkaline pullulanase B. Bacillus sp. KSM-AP 1378 (FERM BP-3048) which is a microoganism capable of producing alkaline pullulanase B was thus obtained.

| Medium C | Pullulan | 0.5% |
|---|---|---|
| | Soluble Starch | 0.5 |
| | Colored Pullulan | 0.2 |
| | Colored Starch | 0.2 |
| | Polypeptone | 0.2 |
| | Yeast extract | 0.1 |
| | $KH_2PO_4$ | 0.03 |
| | $(NH_4)_2SO_4$ | 0.1 |
| | $MgSO_4.7H_2O$ | 0.02 |
| | $CaCl_2.2H_2O$ | 0.02 |
| | $FeSO_4.7H_2O$ | 0.001 |
| | $MnCl_2.4H_2O$ | 0.0001 |
| | Agar | 1.5 |
| | $Na_2CO_3$ | 0.5 |
| | pH 10.0 | |
| Medium D | Pullulan | 0.5% |
| | Soluble Starch | 0.5 |
| | Tryptone | 0.2 |
| | Yeast extract | 0.1 |
| | $KH_2PO_4$ | 0.03 |
| | $(NH_4)_2SO_4$ | 0.1 |
| | $MgSO_4.7H_2O$ | 0.02 |
| | $CaCl_2.2H_2O$ | 0.02 |
| | $FeSO_4.7H_2O$ | 0.001 |
| | $MnCl_2.4H_2O$ | 0.0001 |
| | $Na_2CO_3$ | 0.5 |
| | pH 10.0 | |

2) The strains of Bacillus sp. KSM-AP 1378 which produce alkaline pullulanase B having α-amylase activity were inoculated into the liquid Medium D, and shake-caltivated at 30° C. for 3 days. After the cultivation, cells were centrifugally separated to obtain a crude enzyme solution, which was processed according to a conventional method to prepare ethanol-dried powder. A crude enzyme sample shown in Table 6 was obtained. Enzymatic activities were measured at pH 9.

TABLE 6

| Strain | Amount of crude enzyme per 1 l of medium (g) | Enzyme activity (U/g) Pullulanase | α-amylase |
|---|---|---|---|
| KSM-AP 1378 | 0.2 | 2096 | 2476 |

Figure 12:
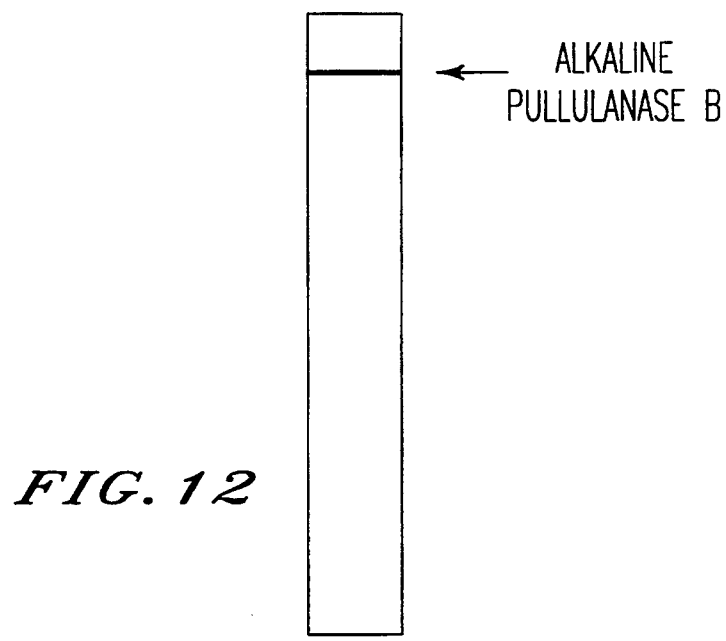
FIG. 12 is an electrophoresis profile of the alkaline pullulanase B having α-amylase activity used in the present invention according to the method of Davis.

3) To a supernatant of the crude enzyme prepared in 2) was added DEAE-cellulose powder, and pullulanase in the supernatant was completely adsorbed onto the DEAE-cellulose. After the resin was washed with 10 mM tris-HCl buffer solution (pH 8), the enzyme was eluted with 10 mM tris-HCl buffer solution (pH 8) containing 0.6M NaCl. The eluate was dialyzed against 10 mM tris-HCl buffer solution (pH 8). Then, the enzyme was adsorbed onto an α-cyclodextrin affinity column equilibrated with 10 mM tris-HCl buffer solution, and eluted with 10 mM tris-HCl buffer solution (pH 8) containing β-cyclodextrin to collect active fractions. After dialyzing, the active fractions were adsorbed to DEAE Toyopearl 650 S (trade-mark) equilibrated with 1.0 mM tris-HCl buffer solution (pH 8). The enzyme adsorbed was gradiently eluted with 10 mM tris-HCl buffer containing NaCl having concentration of 0.1-1M to collect active fractions. After dialyzing, the active fractions were filled into a Sephacryl S-200 column equilibrated with 10 mM tris-HCl buffer solution (pH 8) containing 0.1M NaCl and eluted with the same buffer containing 0.1M NaCl to collect active fractions. The collected active fractions were concentrated on an ultrafiltration membrane and dialyzed overnight against 10 mM tris-HCl buffer solution (pH 8) to obtain alkaline pullulanase B having α-amylase activity. The obtained alkaline pullulanase B was subjected to electrophoresis according to the method of Davis [Davis D. J., Ann. N.Y. Acad. Sci., 121, 404, (1964)], and stained with Coomassie Brilliant Blue to confirm that it gave a single band (FIG. 12).

5) The alkaline pullulanase B having α-amylase activity obtained in 4) was subjected to sodium dodecyl sulfate (SDS) electrophoresis according to a conventional method. The results are shown in FIG. 13. It was confirmed that the enzyme had a molecular weight of 200,000±5,000. Example 1 (Detergent for automatic dish-washer)

Washing conditions, detergency tests, and the results were as follows.

1) Washing conditions

| Washing machine used | All-automatic dish-washer (NP-600, manufactured by Matsushita Electrical Industry Co.). This machine is of the type that a detergent solution is jet-sprayed from a rotary nozzle and washes the dishes arranged above the jet orbit of the detergent solution. |
|---|---|
| Washing temperature | Temperature was raised slowly from 5° C. to 55° C.. |
| Water for washing | Water hardness = 3.5° DH |
| Detergent concentration: | 0.2% |
| Washing time | Washing: 20 minutes, Rinsing: 20 minutes. |
| Amount of circulated water during washing: | 2.5 l |

2Evaluation of detergency

Dishes contaminated by starch soil and the evaluation method:

Contaminated Dishes

Rice flour and boiled rice grains were mixed (9:1), and further mixed with a mixer after adding an equal amount of tap water. The above soil (4 g) was applied uniformly onto porcelain dishes having a diameter of 22 cm, and air-dried for one whole day and night.

The above 8 dishes were subjected to a detergency test.

The Evaluation Method for Detergency Against Starch Soil

Remaining starch on the dishes was measured by a photograph to determine the blue-part-area (P1) generated by iodo-color-reaction. Then, washing rate was obtained from the above P1 and the initial contamination area (So) by the following equation.

Detergency rate = $[(S_o - P_1)/S_o] \times 100$

3) Washing composition

| | | |
|---|---|---|
| Softanol EP 7045 (manufactured by Nippon Shokubai Kagaku Industry Co.) | 2 wt. % | |
| Sodium citrate | 20 | |
| No. 1 sodium silicate | 5 | |
| Enzyme | See Table 7 | |
| Sodium Carbonate | balance | |

(Note)
Values for enzymes give activities in the detergent composition.

4) Results of detergency test

The results are shown in Table 7.

TABLE 7

| | | Samples of present invention | | Comparative Compositions | |
|---|---|---|---|---|---|
| | | 1 | 2 | 1 | 2 |
| Enzyme activity (U/g) | Alkaline pullulanase A | 100 | 250 | — | — |
| | Promozyme | — | — | 500 | — |
| | Termamyl 60 T | — | — | — | 500 |
| | Detergency (%) | 60 | 70 | 20 | 30 |

(Notes)
Alkaline pullulanase A was obtained in preparation Example 1.
Promozyme is a pullulanase manufactured by Novo Co.
Termamyl 60 T is an α-amylase manufactured by Novo Co.

Enzyme activities shown in Table 7 were measured by the method below.

As for the 2 kinds of pullulanases, 0.1 ml of enzyme solution was added to a 0.9 ml substrate solution consisting of 10 mM glycine-NaCl-NaOH buffer solution (pH 9.0) and pullulan (final concentration in the reaction system was 0.25%) to react at 40° C. for 30 minutes. As for Termamyl 60T, 0.1 ml of enzyme solution was added to a 0.9 ml of substrate solution consisting of 10 mM glycine-NaCl-NaOH buffer solution (pH 9.0) and soluble starch (final concentration in the reaction system was 0.25%) to react at 50° C. for 15 minutes. After the reaction, quantitative determination of the reducing sugar was carried out by the method of 3,5-dinitrosalicylic acid (DNS). Specifically, 1.0 ml of DNS reagent was added to 1.0 ml of reaction mixture, and the mixture was heated at 100° C. for 5 minutes to develop color. After cooling, the mixture was diluted with 4.0 ml of deionized water. This solution was subjected to colorimetric quantitative analysis at wave length of 585 nm. One unit (1 U) of enzyme activity was defined to be the amount of enzyme which released 1 μmol of reducing sugar (as glucose) per minute.

Example 2 (Detergent for Clothes)

Washing conditions, detergency tests, and the results were as follows.

1) Artificially contaminated cloths (test material)

Rice flour and boiled rice grains were mixed (9:1), and further mixed with a mixer after adding an equal amount of tap water. The above solution was applied onto a 10 cm×10 cm of a cotton cloth in an amount of 2.5-5% by weight based on the weight of the cloth, then dried at 20° C. for 24 hours.

2) Washing conditions and method

A detergent composition was dissolved into a hard water of 4° DH to prepare a 0.665% detergent solution. Five pieces of artificially-contaminated cotton cloths were placed in the detergent solution. After allowing it to stand at 40° C. for one hour, they were transferred to the stainless beaker to wash at 100 rpm, 20° C., for 10 minutes with a Terg-O-Tometer. After rinsing with running water, the cloths were dried at 20° C., for 24 hours, and subjected to quantitative measurement.

3) Evaluation of detergency

The weights of the original cloths and the contaminated cloths before and after washing were measured. Detergency rate (%) was calculated by the following equation.

$$\text{Detergency rate (\%)} = \frac{\text{Weight before washing} - \text{Weight after washing}}{\text{Weight before washing} - \text{Weight of original cloth}} \times 100$$

Values of detergency in Table 8 are averages of 5 pieces.

4) Detergent composition

| | |
|---|---|
| Sodium linear dodecylbenzene sulfonate | 15 wt. % |
| Sodium alkylethoxy sulfate ($C_{14}$-$C_{15}$, EO = 3 mol) | 5 |
| 4A-type zeolite | 15 |
| Sodium silicate | 15 |
| Sodium carbonate | 15 |
| Sodium polyacrylate (MW = 8000) | 1.5 |
| Polyethylene glycol (MW = 6000) | 1.5 |
| Enzyme | Table 8 |
| Fluorescent dye | 0.5 |
| Glauber's salt | balance |
| Water | 5 |

(notes)
Values for enzymes give activities in the detergent composition.

5) Results of detergency tests

The results are shown in Table 8.

TABLE 8

| | | Samples of present invention | | Comparative Compositions | |
|---|---|---|---|---|---|
| | | 3 | 4 | 3 | 4 |
| Enzyme activity (U/g) | Alkaline pullulanase A | 100 | 250 | — | — |
| | Promozyme | — | — | 500 | — |
| | Termamyl 60 T | — | — | — | 500 |
| | Detergency (%) | 50 | 70 | 25 | 40 |

The measurement of enzyme activities in Table 8 was the same as explained the data in Table 7.

Example 3 (Detergent Composition for an Automatic Dishwasher)

Detergency test was carried out in the same manner as in Example 1 except for using alkaline pullulanase B as an enzyme.

The results are shown in Tables 9 and 10.

TABLE 9

| | | Samples of present invention | | Comparative Compositions |
|---|---|---|---|---|
| | | 5 | 6 | 5 |
| Enzyme activity (U/g) | Alkaline pullulanase B | 7 | 14 | — |
| | Termamyl 60 T | — | — | 14 |
| | Detergency (%) | 60 | 80 | 50 |

(notes)
Alkaline pullulanase B was obtained in Preparation Example 2.
Termamyl 60 T is an α-amylase manufactured by Novo Co.

Enzyme activities shown in Table 9 were measured by the method of "Amylase B-test Wako" (CM-amylose DEX method). 1U was defined to be an enzyme unit where 100 ml of enzyme decomposes the right amounts of 10 mg of starch.

TABLE 10

|  |  | Samples of present invention | | Comparative Compositions |
|---|---|---|---|---|
|  |  | 7 | 8 | 6 |
| Enzyme activity (U/g) | Alkaline pullulanase B | 50 | 80 | — |
|  | Promozyme | — | — | 200 |
|  | Detergency (%) | 60 | 80 | 30 |

(notes)
Alkaline pullulanase B was obtained in Preparation Example 2.
Promozyme is a pullulanase manufactured by Novo Co.

Enzyme activities shown in Table 10 were measured by the following method.

A 0.1 ml enzyme solution was added to 0.9 ml of a substrate solution consisting of 10 mM glycine-NaCl-NaOH buffer solution (pH 9.0) and pullulan (final concentration in the reaction system was 0.25%) which was to react at 40° C. for 30 minutes. After the reaction, quantitative determination of reducing sugar was carried out by the method of 3,5-dinitro salicylic acid (DNS). In detail, 1.0 ml of DNS reagent was added to 1.0 ml of the reaction mixture, and the mixture was heated at 100° C. for 5 minutes to develop color. After cooling, the mixture was diluted with 4.0 ml of deionized water. This solution was subjected to colorimetric quantitative analysis at wave length of 535 nm.

One unit (1U) of enzyme activity was defined to be the amount of enzyme which released 1 μmol of reducing sugar (as glucose) per minute.

Example 4 (Detergent Composition for Clothes)

Detergents of the following compositions were prepared. Detergency test was carried out in the same manner as in Example 2.

1) Detergent composition

| Sodium linear dodecylbenzene sulfonate | 15 wt. % |
|---|---|
| Sodium alkylethoxy sulfonate ($C_{14}$–$C_{15}$, EO = 3 mol) | 5 |
| 4A type zeolite | 15 |
| Sodium silicate | 15 |
| Sodium carbonate | 15 |
| Sodium polyacrylate (MW = 8000) | 1.5 |
| Polyethyleglycol (MW = 6000) | 1.5 |
| Enzyme | Table 11 or Table 12 |
| Fluorescent dye | 0.5 |
| Glauber's salt | balance |
| Water | 5 |

(notes)
Values for enzymes mean activities in the detergent composition.

2) Results of detergency test
The results are shown in Tables 11 and 12.

TABLE 11

|  |  | Samples of present invention | | Comparative Compositions |
|---|---|---|---|---|
|  |  | 9 | 10 | 7 |
| Enzyme activity (U/g) | Alkaline pullulanase B | 8 | 14 | — |
|  | Termamyl 60 T | — | — | 14 |
|  | Detergency (%) | 65 | 80 | 50 |

(notes)
Alkaline pullulanase B was obtained in Preparation Example 2.
Termamyl 60T is an α-amylase manufactured by Novo Co.

Enzyme activities shown in Table 11 were measured by the method explained for Table 9 data.

TABLE 12

|  |  | Samples of present invention | | Comparative Compositions |
|---|---|---|---|---|
|  |  | 11 | 12 | 8 |
| Enzyme activity (U/g) | Alkaline pullulanase B | 50 | 80 | — |
|  | Termamyl 60 T | — | — | 250 |
|  | Detergency (%) | 55 | 80 | 35 |

(notes)
Alkaline pullulanase B was obtained in Preparation Example 2.
Promozyme is a pullulanase manufactured by Novo Co.

Enzyme activities shown in Table 12 were measured by the method explained for Table 10 data.

As explained above, the detergent compositions of the present invention exhibited an excellent detergency against starch soils within a normal operation time.

Example 5 (Detergent Composition for Automatic Dish Washer)

The following detergent composition was prepared.

| (Composition) | |
|---|---|
| Softanol EP-7085 [1] | 4.5 wt. % |
| Trisodium citrate | 20.0 |
| Sokalan CP-5 powder [2] | 5.0 |
| Lipase [3] | 1.0 |
| Alkaline Pullulanase A [4] | 250 [4] |
| Sodium hydrogencarbonate | 50.0 |
| Sodium sulfate | balance |

Note)
[1] Softanol EP-7085: Addition product of sec-alcohol added with 7 mols of ethylene oxide and 8.5 mols of propylene oxide manufactured by Nippon Shokubai Kagaku Kogyo K.K.
[2] Sokalan CP-5 powder: Salt of copolymer of acrylic acid and maleic anhydride, MW = about 70,000 (manufactured by BASF)
[3] Lipase AKG: Manufactured by Amano Seiyaku K.K.
[4] Alkaline pullulanase: Obtained in Preparation Example 1. The given value indicates the activity (Unit/g detergent) of one gram of detergent.

Example 6 (Detergent Composition for Automatic Dish Washer)

The following detergent composition was prepared.

| (Composition) | |
|---|---|
| Pluronic L92 [5] | 4 wt. % |
| Trisodium citrate | 30 |
| Lipase [6] | 1.5 |
| Alkaline pullulanase B [7] | 80 [7] |
| Sodium hydrogencarbonate | 30 |
| Sodium metasilicate | 2 |
| Sodium sulfate | balance |

Note)
[5] Pluronic L92: Polyoxyethylene-polyoxypropylene block copolymer, average molecular weight = 3,500 (manufactured by Asahi Denka K.K.)
[6] Lipolase 30T: Manufactured by Novo Industry Co.
[7] Obtained in Preparation Example 2. The given value indicates the activity (Unit/g detergent) of one gram of detergent.

The detergent compositions of Examples 5 and 6 exhibited excellent detergency not only against starch soils, but also against complex stains of starch soil, fats and oils and protein soils.

Obviously, numerous modifications and variations of the present invention are possible in light of the above teachings. It is therefore to be understood that within the scope of the appended claims the present invention may be practiced otherwise than as specifically described herein.

What is claimed is:

1. A detergent composition comprising from 0.5 to about 10 wt. % of an alkaline pullulanase which has an optimum pH in the alkaline range, wherein said alkaline pullulanase has the following enzymological characteristics:

1) Action
   Decomposes α-1,6 glucoside linkage of pullulan to produce maltotetraose, and hydrolyzes α-1,6 glucoside linkage of starch, amylopectin, glycogen or their partial decomposition products;
2) Substrate specificity
   Hydrolyzes a branching structure having a degree of polymerization not less than the degree of polymerization of maltose among sugars having a branching structure branched at an α-1,6 glucoside linkage;
3) Working pH and optimum PH range
   The working pH being in the range of 5–11 with the optimum pH in the range of 9.5–11;
4) pH stability
   Quite stable in the pH range of 8–10, and has not less than 50% of relative activity even in the pH range of 7–10.5 (treatment conditions: 45° C., 10 minutes);
5) Working temperature and optimum temperature
   Acts at the temperature range of 10°–60° C. with an optimum temperature being about 50° C;
6) Thermal stability
   Quite stable up to 40° C. when treated in 10 mM glycine-NaCl-NaOH buffer solution (pH 9.5) for 30 minutes;
7) Effects of surfactants
   Activities being scarcely adversely affected by surfactants such as linear alkylbenzene sulfonate, sodium alkyl sulfate, sodium polyoxyethylene alkyl sulfate, sodium α-olefin sulfonate, sodium α-sulfonated fatty acid ester, sodium alkyl sulfonate, sodium dodecyl sulfate, soaps and Softanol (trade-mark), and from 0..5 to 60 wt. % of one or more surfactants.

2. A detergent composition as claimed in claim 1, wherein said alkaline pullulanase has the following enzymological characteristics:

1) Action
   Decomposes α-1,6 glucoside linkage of pullulan to produce maltotriose, and hydrolyzes α-1,6 glucoside linkage of starch, amylopectin, glycogen or their partial decomposition products;
2) Substrate specificity
   Hydrolyzes a branching structure having a degree of polymerization not less than the degree of polymerization of maltose among sugars having a branching structure branched at an α-1,6 glucoside linkage;
3) Working pH and optimum pH range
   The working pH is in the range of 5–11 with the optimum pH in the range of 9.5–11;
4) pH stability
   Quite stable in the pH range of 8–10, and has not less than 50% of relative activity even in the pH range of 7–10.5 (treatment conditions: 45° C., 10 minutes);
5) Working temperature and optimum temperature
   Acts at the temperature range of 10°–60° C. with an optimum temperature being about 50° C.;
6) Thermal stability
   Quite stable up to 40° C. when treated in 10 mM glycine-NaCl-NaOH buffer solution (pH 9.5) for 30 minutes;
7) Molecular weight
   120,000±5,000 determined by sodium dodecyl sulfate (SDS) electrophoresis.
8) Effects of metal ions
   Activities being adversely affected by $Hg^{2+}$, $Cd^{2+}$, $Mn^{2+}$, and $Pb^{2+}$;
9) Effects of surfactants
   Activities being scarcely adversely affected by surfactants such as linear alkylbenzene sulfonate, sodium alkyl sulfate, sodium polyoxyethylene alkyl sulfate, sodium α-olefin sulfonate, sodium α-sulfonated fatty acid ester, sodium alkyl sulfonate, sodium dodecyl sulfate, soaps, and Softanol (trademark);
10) Effects of chelating agents
    Activities being scarcely adversely affected by chelating agents such as EDTA, EGTA, citric acid, and zeolite;
11) Resistance of protease
    Has strong resistance to alkaline protease.

3. A detergent composition as claimed in claim 1, wherein said alkaline pullulanase is separated from a culture of a microorganism belonging to genus Bacillus.

4. A detergent composition as claimed in claim 3, wherein said microorganism is Bacillus sp. KSM-AP 1876 deposited as FERM BP-3049.

* * * * *

UNITED STATES PATENT AND TRADEMARK OFFICE
CERTIFICATE OF CORRECTION

PATENT NO. : 5,429,766
DATED : July 4, 1995
INVENTOR(S) : Taeko SONE, et al.

It is certified that error appears in the above-indentified patent and that said Letters Patent is hereby corrected as shown below:

On the title page, Item [54], and Column 1, Lines 1 and 2, the title should read:

--DETERGENT COMPOSITION CONTAINING ALKALINE PULLULANASE ENZYME--

Signed and Sealed this

Twenty-ninth Day of August, 1995

Attest:

BRUCE LEHMAN

*Attesting Officer*   *Commissioner of Patents and Trademarks*